United States Patent
Sase

(10) Patent No.: US 10,996,147 B2
(45) Date of Patent: May 4, 2021

(54) SAMPLE PREPARATION METHOD AND SAMPLE PREPARING APPARATUS

(71) Applicant: NIKON CORPORATION, Tokyo (JP)

(72) Inventor: Ichiro Sase, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 75 days.

(21) Appl. No.: 16/105,092

(22) Filed: Aug. 20, 2018

(65) Prior Publication Data

US 2018/0356321 A1 Dec. 13, 2018

Related U.S. Application Data

(63) Continuation of application No. PCT/JP2016/054966, filed on Feb. 19, 2016.

(51) Int. Cl.

| | |
|---|---|
| *G01N 1/30* | (2006.01) |
| *G01N 1/44* | (2006.01) |
| *G01N 23/225* | (2018.01) |
| *G01N 23/04* | (2018.01) |
| *H01J 37/20* | (2006.01) |
| *G02B 21/36* | (2006.01) |
| *G02B 21/00* | (2006.01) |
| *G02B 21/06* | (2006.01) |
| *G01N 1/42* | (2006.01) |
| *C12M 1/12* | (2006.01) |
| *G01N 21/64* | (2006.01) |

(52) U.S. Cl.
CPC .............. *G01N 1/30* (2013.01); *C12M 25/00* (2013.01); *G01N 1/42* (2013.01); *G01N 1/44* (2013.01); *G01N 23/225* (2013.01); *G02B 21/0088* (2013.01); *G02B 21/06* (2013.01); *G02B 21/361* (2013.01); *H01J 37/20* (2013.01); *G01N 21/6428* (2013.01); *G01N 23/04* (2013.01)

(58) Field of Classification Search
None
See application file for complete search history.

(56) References Cited

U.S. PATENT DOCUMENTS

| | | |
|---|---|---|
| 2007/0120069 A1 | 5/2007 | Takamizawa |
| 2009/0126373 A1 | 5/2009 | Burg |
| 2011/0116165 A1 | 5/2011 | Suzuki |
| 2013/0089856 A1 | 4/2013 | Soddu et al. |
| 2013/0227970 A1 | 9/2013 | Lihl et al. |
| 2015/0323775 A1 | 11/2015 | Suzuki |

FOREIGN PATENT DOCUMENTS

| | | |
|---|---|---|
| JP | 2011-508185 A | 3/2011 |
| JP | 2011-107257 A | 6/2011 |
| JP | 2012-155299 A | 8/2012 |
| JP | 2013-181987 A | 9/2013 |
| WO | 2017/141447 A1 | 8/2017 |

OTHER PUBLICATIONS

Faas et al., "Localization of fluorescently labeled structures in frozen-hydrated samples using integrated light electron microscopy", Journal of Structural Biology, vol. 181, pp. 283-290). (Year: 2013).*
Apr. 28, 2020 Office Action issued in Japanese Patent Application No. 2019-162279.
Oct. 1, 2019 Search Report issued in European Patent Application No. 16890587.5.
May 17, 2016 International Search Report issued in International Patent Application No. PCT/JP2016/054966.
May 17, 2016 Written Opinion issued in International Patent Application No. PCT/JP20161054966.
Sep. 8, 2020 Office Action issued in Japanese Patent Application No. 2019-162279.

* cited by examiner

*Primary Examiner* — Michelle F. Paguio Frising
(74) *Attorney, Agent, or Firm* — Oliff PLC

(57) ABSTRACT

A sample preparation method includes: irradiating a first region of a sample with light at a time t1; irradiating a second region different from the first region with the tight at a time t2 after the time t1; and fixing the sample at a time t3 after the time t2. A sample preparing apparatus includes: a light radiating unit that irradiates a first region of a sample with light at time t1 and irradiates a second region different from the first region with the light at a time t2 after the time t1; and a fixing unit that fixes the sample at a time t3 after the time t2.

13 Claims, 22 Drawing Sheets

| | | | |
|---|---|---|---|
| 146— | NO. OF REGS | 4 | —147 |

| | | | |
|---|---|---|---|
| | STIMUL INTERVAL | 200 msec | —154 |
| | STIMUL DURATION | 10 msec | —180 |
| 146— | STIMUL TIME #1 | 0 msec | —155 |
| | #2 | 200 msec | —156 |
| | #3 | 400 msec | —157 |
| | #4 | 600 msec | —158 |

| | | | |
|---|---|---|---|
| 146— | FIX TIME | 810 msec | —159 |

SAMPLE PREPARATION METHOD AND SAMPLE PREPARING APPARATUS

The contents of the following International patent application are incorporated herein by reference:
NO. PCT/JP2016/054966 filed on Feb. 19, 2016.

BACKGROUND

1. Technical Field

The present invention relates to a sample preparation method and a sample preparing apparatus.

2. Related Art

An apparatus that photically stimulates a biological sample and freezes and saves it is known (please see Patent Document 1, for example).
Patent Document 1: US2013/0227970
There is an increasing demand requiring to make it possible to observe samples with an electron microscope under varied conditions about photostimulation of the samples, and samples therefor are required.

SUMMARY

A first aspect of the present invention provides a sample preparation method including: irradiating a first region of a sample with light at a time t1; irradiating a second region different from the first region with the light at a time t2 after the time t1, and fixing the sample at a time t3 after the time t2.

A second aspect of the present invention provides a sample preparation method including: irradiating a first region of a sample and a second region different from the first region with light at a time t1; irradiating the first region with light at a time t2 after the time t1; irradiating the second region with the light at a time t3 after the time t2; and fixing the sample at a time t4 after the time t3.

A third aspect of the present invention provides a sample preparation method including: irradiating a first region of a sample and a second region different from the first region with light for mutually different lengths of time after simultaneously starting the irradiation of light; and fixing the sample after the irradiating.

A fourth aspect of the present invention provides a sample preparing apparatus including: a light radiating unit that irradiates a first region of a sample with light at time t1 and irradiates a second region different from the first region with the light at a time t2 after the time t1; and a fixing unit that fixes the sample at a time t3 after the time t2.

A fifth aspect of the present invention provides a sample preparing apparatus including: a light radiating unit that performs: irradiating a first region of a sample and a second region different from the first region with light at a time t1; irradiating the first region with light at a time t2 after the time t1; and irradiating the second region with the light at a time t3 after the time t2; and a fixing unit that fixes the sample at a time t4 after the time t3.

A sixth aspect of the present invention provides a sample preparing apparatus including: a light radiating unit that irradiates a first region of a sample and a second region different from the first region with light for mutually different lengths of time after simultaneously starting the irradiation of light; and a fixing unit that fixes the sample after the irradiating.

A seventh aspect of the present invention provides a sample preparing apparatus including a display unit that displays a setting screen that allows setting of an order of performing: irradiating a first region of a sample with light; irradiating a second region different from the first region with the light; and fixing the sample.

An eighth aspect of the present invention provides a sample preparing apparatus including a display unit that displays a setting screen that allows setting of: a time at which a first region of a sample is irradiated with light; a time at which a second region different from the first region is irradiated with the light; and a time at which the sample is fixed.

A ninth aspect of the present invention provides a sample preparing apparatus comprising a display unit that displays a setting screen that allows setting of: a time t1 at which a first region of a sample is irradiated with light; a time t2 at which a second region different from the first region is irradiated with tight after the time t1; and a time t3 at which the sample is fixed after the time t2.

The summary clause does not necessarily describe all necessary features of the embodiments of the present invention. The present invention may also be a sub-combination of the features described above.

BRIEF DESCRIPTION OF THE DRAWINGS

FIG. 5 is a figure showing a setting screen 145 for photostimulation conditions.

DESCRIPTION OF EXEMPLARY EMBODIMENTS

Hereinafter, (some) embodiment(s) of the present invention will be described. The embodiment(s) do(es) not limit the invention according to the claims, and all the combinations of the features described in the embodiment(s) are not necessarily essential to means provided by aspects of the invention.

Figure 1:
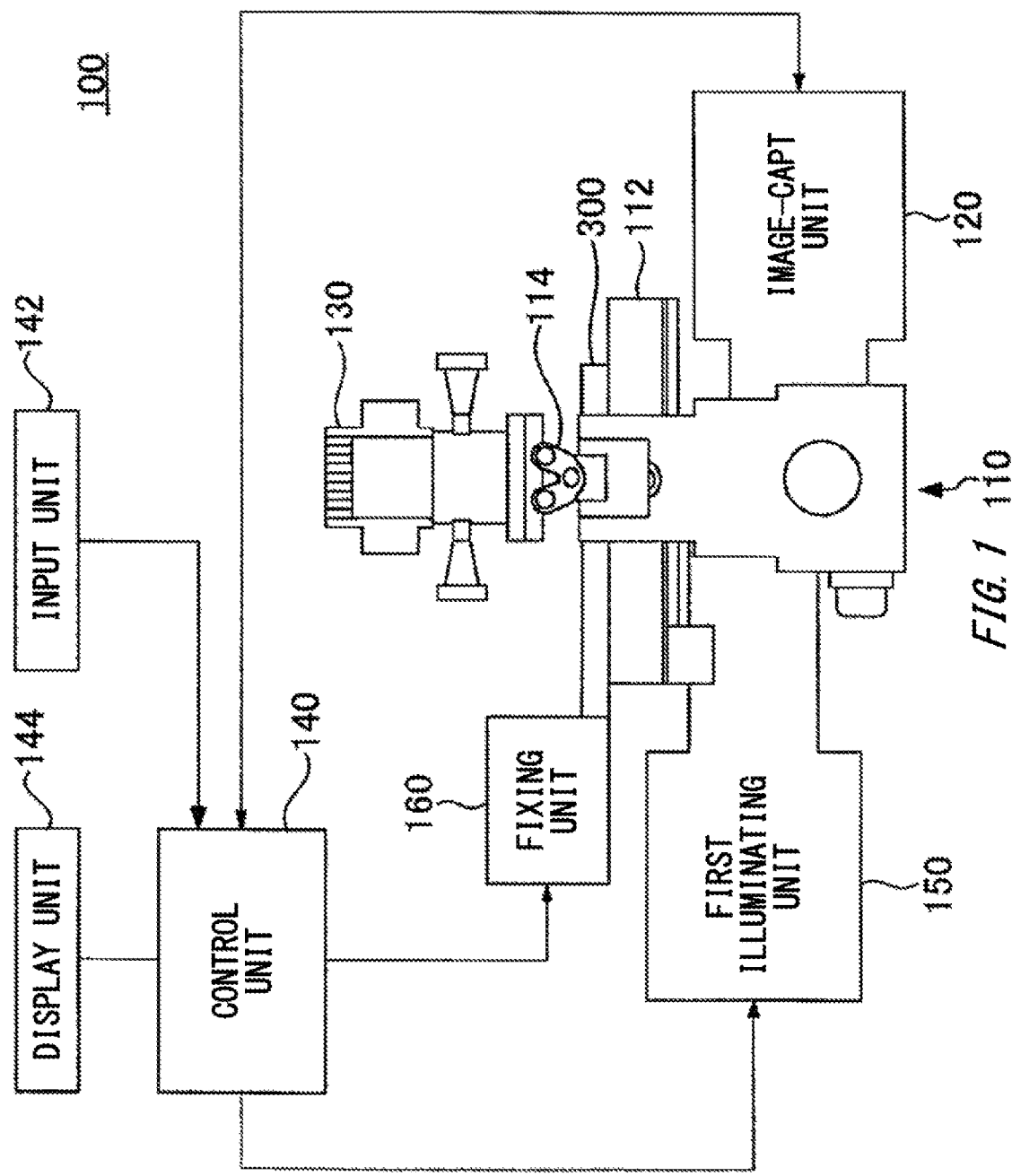
FIG. 1 is a schematic diagram showing an entire sample preparation system 100.

FIG. 1 is a schematic diagram of an entire sample preparation system 100. The sample preparation system 100 includes an inverted microscope 110, an image-capturing unit 120, a second illuminating unit 130, a control unit 140, an input unit 142, a display unit 144, a first illuminating unit 150 and a fixing unit 160.

The inverted microscope 110 has a stage 112 and an eyepiece unit 114. The stage 112 supports and positions a sample to be an observation target. In the example shown in the figure, a sample held by a sample holder 300 is placed on the stage 112. The sample placed on the stage 112 is observed from the eyepiece unit 114.

The image-capturing unit 120 has image sensors such as CCD or CMOS sensors, and records an image of a sample observed using the inverted microscope 110. The second illuminating unit 130 radiates illumination light toward a sample placed on the stage 112.

The control unit 140 controls operation of each unit of the sample preparation system 100, and additionally accepts setting of and instructions to each unit of the sample preparation system 100 through the input unit 142. In addition, the control unit 140 displays, on the display unit 144, a setting screen for accepting setting of and instructions to each unit of the sample preparation system 100. The control unit 140 controls at least the first illuminating unit 150 and fixing unit 160 based on information set on the setting screen. The control unit 140 may be formed of dedicated hardware or may be formed by implementing a program written for the sample preparation system 100 on a general-purpose apparatus such as a personal computer.

The first illuminating unit 150 irradiates a sample on the stage 112 with stimulating light and excitation light.

One example of photostimulation may be to irradiate a caged compound with light to uncage and activate it, and trigger a particular reaction of cells or to irradiate channelrhodopsins with light to cause ions to flow into cells in optogenetics, but these are not the only examples. For example, it may be to photobleach, photoconvert or photoactivate fluorochromes by irradiating them with light.

The fixing unit 160 operates under the control of the control unit 140 to fix the state of a sample placed on the stage 112. For example, it can fix the state of a sample stimulated by the first illuminating unit 150 at timing as instructed by the control unit 140. In the following explanation, to "fix" means to stop a chemical reaction or biological reaction so that the composition of a sample or the like no longer changes. In addition, to "fix" also includes to prevent migration, deformation or the like of cells using cross-linked compositions.

The method used by the fixing unit 160 to fix the state of a sample is selected as appropriate according to the purpose of observation. Because of this, operation of the fixing unit 160 also varies according to the selected fixation method. For example, if a sample is fixed by freezing, the fixing unit 160 supplies a refrigerant such as liquid nitrogen to the sample. In addition, if a sample is fixed using a chemical solution such as a glutaraldehyde solution, the fixing unit 160 replaces a sample solution with the chemical solution such as a glutaraldehyde solution. Photocurable resin may be used to fix a sample, and in such a case a light radiating unit to cure the resin may be further provided.

Figure 2:
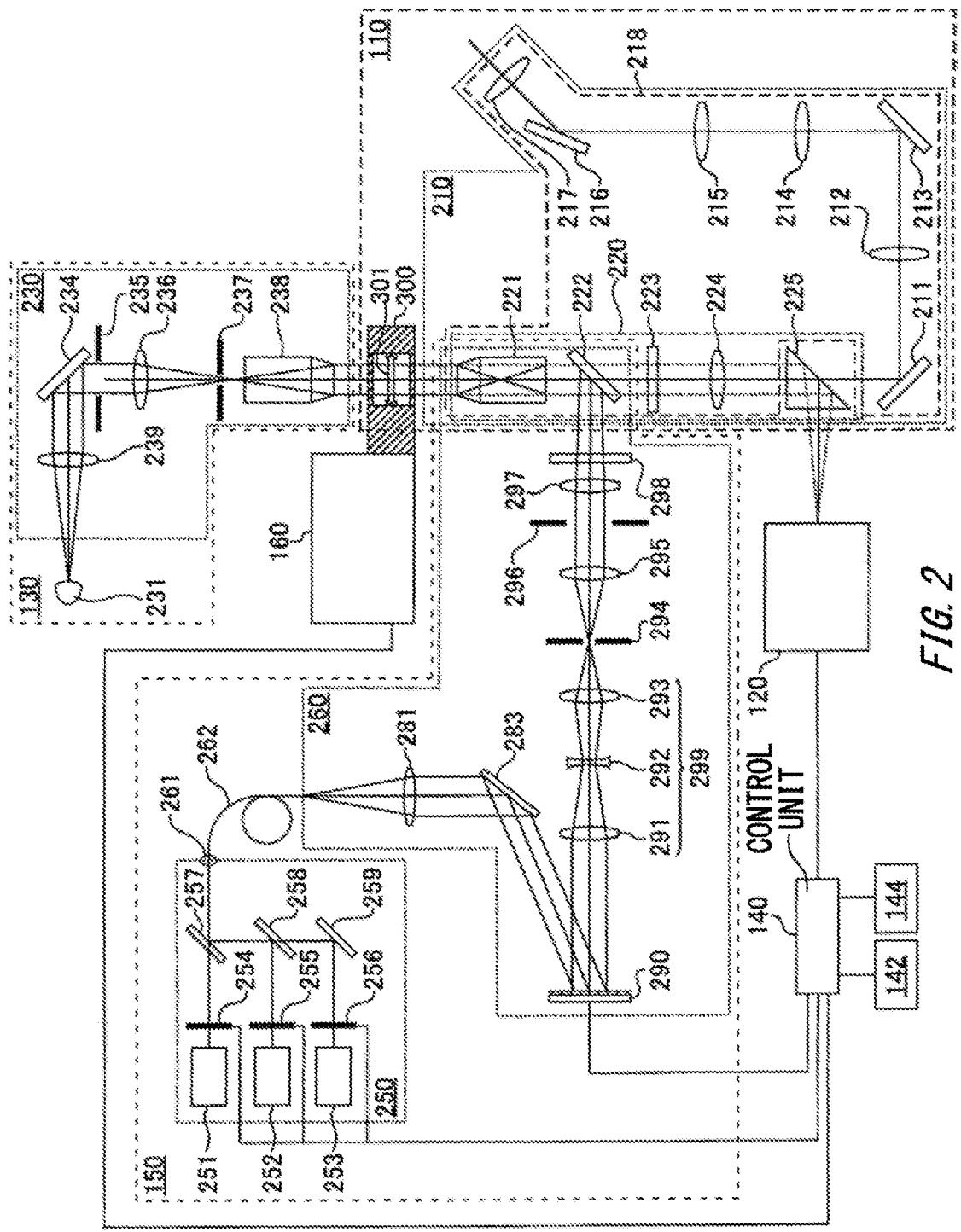
FIG. 2 is a diagram showing optical paths in the sample preparation system 100.

FIG. 2 is an optical path diagram of the sample preparation system 100. The first illuminating unit 150 includes a light source unit 250 and an illumination optical system 260.

The light source unit 250 has: a first light source 251, a second light source 252 and a third light source 253; shutters 254, 255, 256; and dichroic mirrors 257, 258 and a reflecting mirror 259.

Light emitted from the first light source 251 and second light source 252 is used as excitation light for observing fluorescence of a sample 301. In addition, light emitted from the third light source 253 is used as stimulating light for stimulating the sample 301. The wavelength of excitation light is 561 nm, for example. The wavelength of stimulating light is 340 nm, for example.

The shutter 254 and dichroic mirror 257 are disposed on the emission side of the first light source 251. The shutter 254 is opened and closed under the control of the control unit 140, and selectively transmits excitation light emitted from the first light source 251. Likewise, the shutter 255 and dichroic mirror 258 are disposed on the emission side of the second light source 252, and the shutter 255 is opened and closed under the control of the control unit 140, and selectively transmits excitation light emitted from the second light source 252. The shutter 256 and reflecting mirror 259 are disposed on the emission side of the third light source 253, and the shutter 256 is opened and closed under the control of the control unit 140 and selectively transmits stimulating light emitted from the third light source 253.

The reflecting mirror 259 has a characteristic of reflecting stimulating light emitted from the third light source 253. The dichroic mirror 258 has a characteristic of transmitting stimulating light reflected by the reflecting mirror 259, and reflecting excitation light emitted from the second light source 252. The dichroic mirror 257 has a characteristic of transmitting excitation light emitted from the first light source 251, and reflecting excitation light emitted from the second light source 252 and stimulating light emitted from the third light source 253.

In other words, optical paths of excitation light emitted from the first light source 251, excitation light emitted from the second light source 252 and stimulating light emitted from the third light source 253 are converged by the dichroic mirrors 257, 258 and reflecting mirror 259.

Excitation light transmitted through the dichroic mirror 257 and excitation light and stimulating light reflected on the dichroic mirror 257 are condensed at an entrance end of an optical fiber 262 by a photocoupler 261 including a condensing lens. In addition, excitation light and stimulating light are guided by the optical fiber 262 to the illumination optical system 260.

Although in the example shown above, light emitted from the first light source 251 and second light source 252 is used as excitation light, and light emitted from the third light source 253 is used as stimulating light, this is not the only example. For example, light emitted from the first light source 251 and second light source 252 may be used as stimulating light, and light emitted from the third light source 253 may be used as excitation light.

The illumination optical system 260 has a collector lens 281, a reflecting mirror 283, a DMD (Digital Micromirror Device) 290, a relay optical system 299, an aperture stop 294, a lens 295, a field stop 296, a field lens 297, a filter 298, a dichroic mirror 222 and an object lens 221. Light emitted from an emission end of the optical fiber 262 becomes collimated light because of the presence of the collector lens 281. The light having become the collimated light is reflected by the reflecting mirror 283 and is guided to the DMD 290.

The DMD 290 is provided at a position which is conjugate with the observation surface of the sample 301 (the front focal position of the object lens 221). The DMD 290 is a MEMS device, and has a plurality of reflection mirrors that change their orientations individually according to signals received from the control unit 140. Electrodes are provided to the rear surfaces of the reflection mirrors, a voltage is applied thereto according to control signals from the control unit 140, and thereby the orientations of the reflection mirrors change. In the state where voltage is not applied (OFF-state), light reflected on the reflection mirrors is not radiated onto the sample 301, and in the state where voltage is applied (ON-state), light reflected on the reflection mirrors is radiated onto the sample 301.

The relay optical system 299 includes lenses 291, 292, 293. The aperture stop 294 is provided at the rear focal position of the relay optical system 299 and the front focal position of the lens 295. In addition, the field stop 296 is provided at the rear focal position of the lens 295 and the front focal position of the field lens 297. Light reflected on the DMD 290 is condensed at the position of the aperture stop 294 by the relay optical system 299 and becomes collimated light because of the presence of the lens 295. The light that has become the collimated light passes through the field stop 296 and is condensed at the pupil position (rear focal position) of the object lens 221 because of the presence of the field lens 297. The filter 298 has a characteristic of transmitting light at the wavelengths of stimulating light and excitation light, and blocking light at other wavelengths. In addition, the dichroic mirror 222 has a characteristic of reflecting light at the wavelengths of stimulating light and excitation light, and transmitting light from the sample 301. The light condensed at the pupil position (rear focal position) of the object lens 221 becomes collimated light and is radiated onto the sample 301.

The second illuminating unit 130 includes an illumination light source 231 and an illumination optical system 230. Illumination light emitted from the illumination light source 231 is radiated through the illumination optical system 230 onto the sample 301 held by the sample holder 300. The illumination optical system 230 has a collector lens 239, a reflecting mirror 234, a field stop 235, a field lens 236, an aperture stop 237 and a condenser lens 238.

Because the illumination light source 231 is arranged at the front focal position of the collector lens 239, light emitted from the illumination light source 231 becomes collimated light because of the presence of the collector lens 239. The light that has become the collimated light is reflected on the reflecting mirror 234, passes through the field stop 235 and is condensed at the aperture stop 237 arranged at the front focal position of the condenser lens 238 by the field lens 236. The light condensed at the front focal position of the condenser lens 238 becomes collimated light because of the presence of the condenser lens 238 and is radiated onto the sample 301. The field stop 235 is arranged at the rear focal position of the collector lens 239 and the front focal position of the field lens 236. In addition, the aperture stop 237 is arranged at the rear focal position of the field lens 236 and the front focal position of the condenser lens 238. In addition, the aperture stop 237 is arranged at a position which is conjugate with the illumination light source 231.

An observation optical system 210 forms an image of the sample 301 on the stage 112. The observation optical system 210 has a first observation optical system 220 to form an image of the sample 301 in the image-capturing unit 120 and a second observation optical system 218 for observing an image of the sample 301 using an eyepiece 217.

The first observation optical system 220 has the object lens 221, the dichroic mirror 222, a filter 223, an imaging lens 224 and an optical path switching member 225. Fluorescence from the sample 301 passes through the object lens 221 and dichroic mirror 222 and enters the filter 223. The filter 223 has a characteristic of selectively allowing passage therethrough of light in a predetermined wavelength band in light from the sample 301. The filter 223 blocks, for example, illumination light, natural light, stray light or the like reflected on the sample 301. Thereby, it eliminates illumination light that could not be fully eliminated at the dichroic mirror 222. An image of light having passed through the filter 223 is formed at the image-capturing unit 120 by the imaging lens 224 after passing through the optical path switching member 225. The optical path switching member 225 is a prism, for example, and is provided to be able to be inserted into and removed from an optical path of the observation optical system 210. The optical path switching member 225 is, for example, inserted into and removed from the optical path of the observation optical system 210 by a drive unit (not shown in the figure) controlled by the control unit 140. The optical path switching member 225 in the state where it is inserted into the optical path of the observation optical system 210 guides fluorescence from the sample 301 to an optical path toward the image-capturing unit 120 by reflecting the fluorescence on its inner surface.

The second observation optical system 218 has the object lens 221, the dichroic mirror 222, the filter 223, the imaging lens 224, reflecting mirrors 211, 213, 216, relay lenses 212, 214, 215 and the eyepiece 217. After passing through the imaging lens 224, light from the sample 301 forms an intermediate image before the relay lens 212, in the state where the optical path switching member 225 is withdrawn from the optical path of the observation optical system 210. This intermediate image forms a secondary image before the eyepiece 217 because of the presence of the relay lenses 212, 214, 215. An observer can observe an image of a sample using the eyepiece 217. The reflecting mirror 211 is arranged between the imaging lens 224 and the relay lens 212, the reflecting mirror 213 is arranged between the relay lens 212 and the relay lens 214, and the reflecting mirror 216 is arranged between the relay lens 215 and the eyepiece 217. The eyepiece 217 forms an optical system of the eyepiece unit 114 in FIG. 1. Although in the case explained above, fluorescence from a sample is observed, light (transmitted light) radiated from the second illuminating unit 130 onto the sample 301 and transmitted through the sample 301 may be observed.

Figure 3:
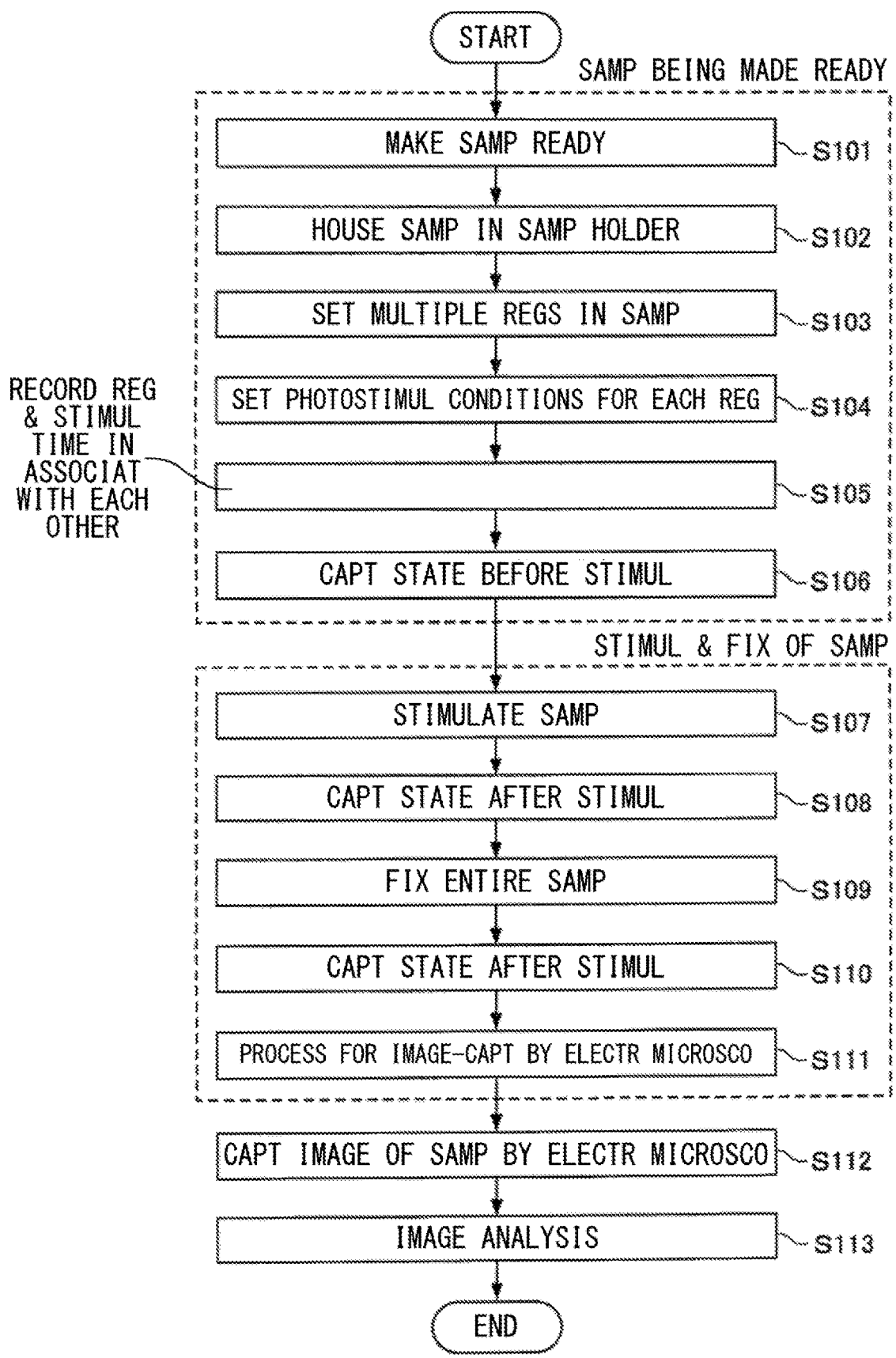
FIG. 3 is a flow diagram showing a procedure of preparing a sample.

FIG. 3 is a flow diagram showing a procedure of preparing, from the sample 301 and using the sample preparation system 100, a sample, an image of which is to be captured by an electron microscope. The procedure shown in FIG. 3 includes: a sample being made ready (Step S101 to Step S106); stimulation and fixation of the sample (Step S107 to Step S111); image-capturing with an electron microscope (Step S112); and image analysis (Step S113). In the following paragraphs, the sample being made ready (Step S101 to Step S106) is explained.

Figure 4:
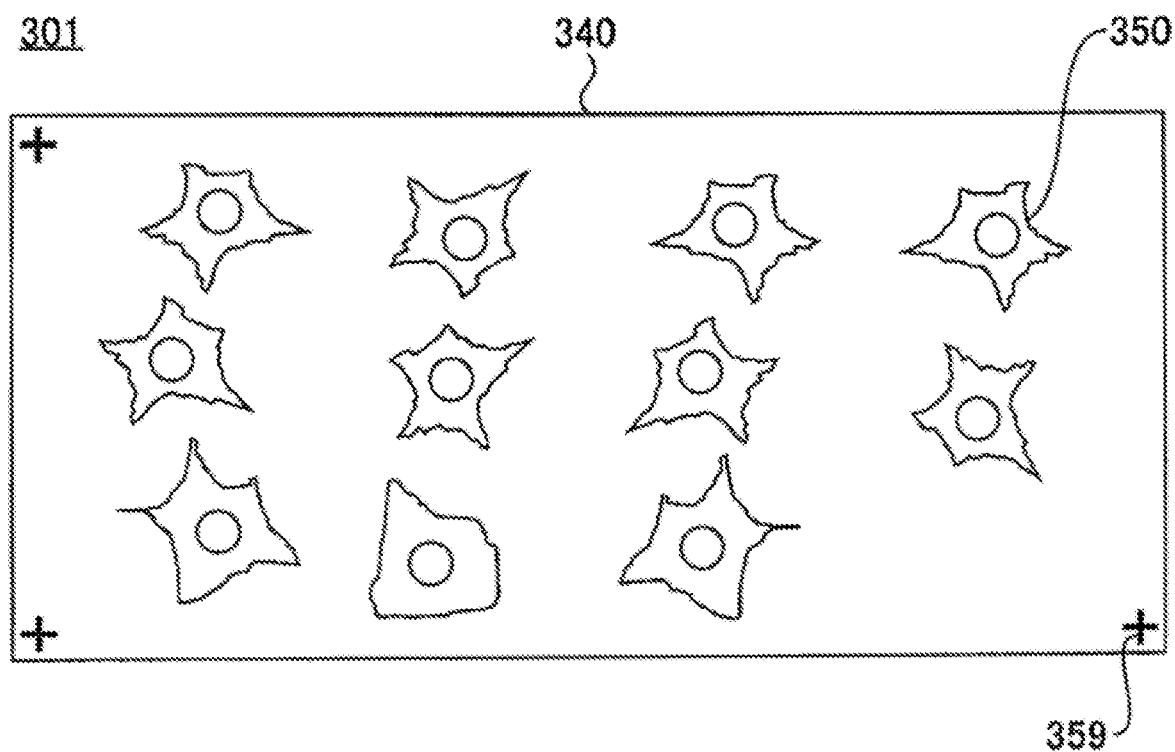
FIG. 4 is a schematic diagram of a sample 301.

First, the sample 301 containing a photoresponsive substance shown in FIG. 4 is made ready as an observation target (Step S101). FIG. 4 is a schematic plan view of the sample 301 to be a material for preparing a sample, an image of which is to be captured by an electron microscope, in the sample preparation system 100. The sample 301 contains a plurality of cells 350 arranged on a support 340, and position indicators 359 are disposed in the support 340. A cover glass to cover the plurality of cells 350 may be placed on the support 340. The sample 301 is housed in the sample holder 300 (please see FIG. 1 (Step S102)). The sample holder 300 housing the sample 301 is placed on the stage 112 of the sample preparation system 100 and joined to the fixing unit 160.

Next, the control unit 140 sets a plurality of regions in the sample 301 (Step S103). In this case, the control unit 140 may set the plurality of regions based on information input via the input unit 142.

FIG. 5 is a figure showing one example of a setting screen 145 displayed on the display unit 144 shown FIG. 1. An input window 147 for a user to input the number of regions to a field 146 about the number of the regions is provided on the setting screen 145. In the example shown in FIG. 5, the state where "4" is input as the number of regions is represented. In the example of the setting screen 145 shown, a time at which a region #1 of a sample is irradiated with light, a time at which a region #2 different from the region #1 is irradiated with light, and a time at which the sample is fixed can be set.

Figure 6:
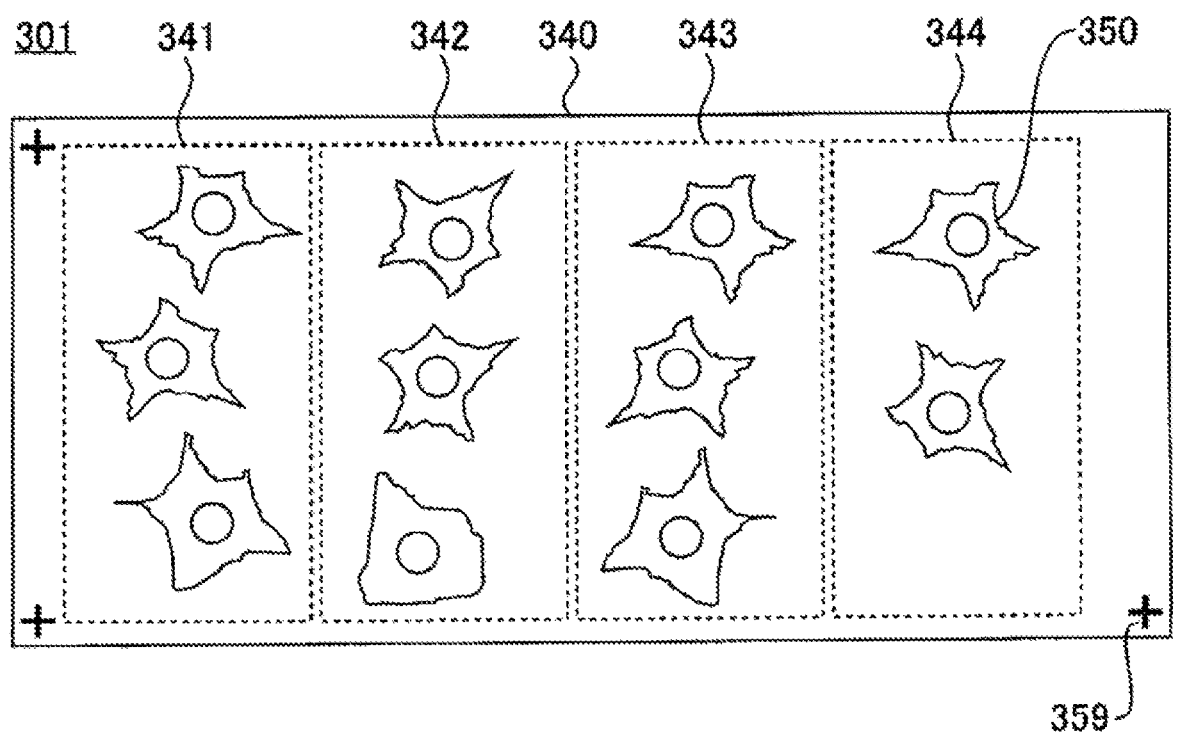
FIG. 6 is a schematic diagram for explaining regions in the sample 301.

FIG. 6 is a schematic diagram showing the state where the control unit 140 has set regions in the sample 301 based on an input to the setting screen 145 shown in FIG. 5. The control unit 140 sets, in a predetermined entire region of the sample, the number of regions based on the number of regions input by a user. For example, in the example shown in FIG. 6, four vertically long rectangular regions 341, 342, 343, 344 of the same size are set from left to right.

Regions set by the control unit 140 preferably do not overlap each other, but may partially overlap. Each of the plurality of regions contains caged compounds or photoresponsive substances such as channelrhodopsin, and stimulating light is radiated onto them region-by-region. Accordingly, gaps may be provided between adjacent regions so that when a predetermined region is irradiated with stimulating light and photically stimulated, adjacent regions are not influenced by the photostimulation. Mechanical partitions or the like are not provided at boundaries between regions set at Step S103.

Next, the control unit 140 sets region-by-region photostimulation conditions for the sample 301 based on information input by a user via the input unit 142 (please see FIG. 5) (Step S104). Here, the photostimulation conditions set for the plurality of regions 341 to 344 include at least two mutually different photostimulation conditions.

Examples of photostimulation conditions set in the above-mentioned manner include a time at which stimulating light is radiated onto each region of the sample 301, a time at which the sample 301 is fixed after stimulation, or the like as shown in FIG. 5. In addition, the light intensity of stimulating light to be radiated, the temperature or atmosphere of the sample 301, or the like may also be set as photostimulation conditions. In the following paragraphs, the above-mentioned photostimulation conditions are further explained with reference to FIG. 5.

Fields 146 for setting the above-mentioned photostimulation conditions are provided on the setting screen 145 shown in FIG. 5. The fields 146 are provided with an input window 154 for inputting a stimulation interval as a temporal interval at which stimulation of each region is started and an input window 180 for inputting stimulation duration during which each region is stimulated. Furthermore, input windows 155, 156, 157, 158 for inputting times at which respective regions are stimulated are also provided in association with the numbers of the respective regions.

If a stimulation interval is input to the input window 154 of the setting screen 145 by a user, the control unit 140 calculates and displays stimulation times of respective regions based on the stimulation interval. In the state shown in the figure, values, 0, 200, 400, 600, are shown in input windows 155 to 158 for the respective regions corresponding to the stimulation interval of 200 milliseconds.

Furthermore, a user may be able to change stimulation times of respective regions from the above-mentioned calculated values. For example, a user can directly input times at which the respective regions are stimulated in the fields 146 to change the stimulation times as appropriate. A user may designate stimulation time without inputting a stimulation interval. In addition, a user also can perform setting such that a plurality of regions among the regions 341, 342, 343, 344 are photically stimulated simultaneously. In this case, the same stimulation time may be designated for example for the region 1 (#1) and the region 2 (#2).

The lowermost field 146 on the setting screen 145 is provided with an input window 159 to which a time at which the sample 301 is fixed is input.

The stimulation and fixation conditions set on the setting screen as mentioned above are confirmed by pressing a save button 148 on the setting screen 145.

Figure 7:
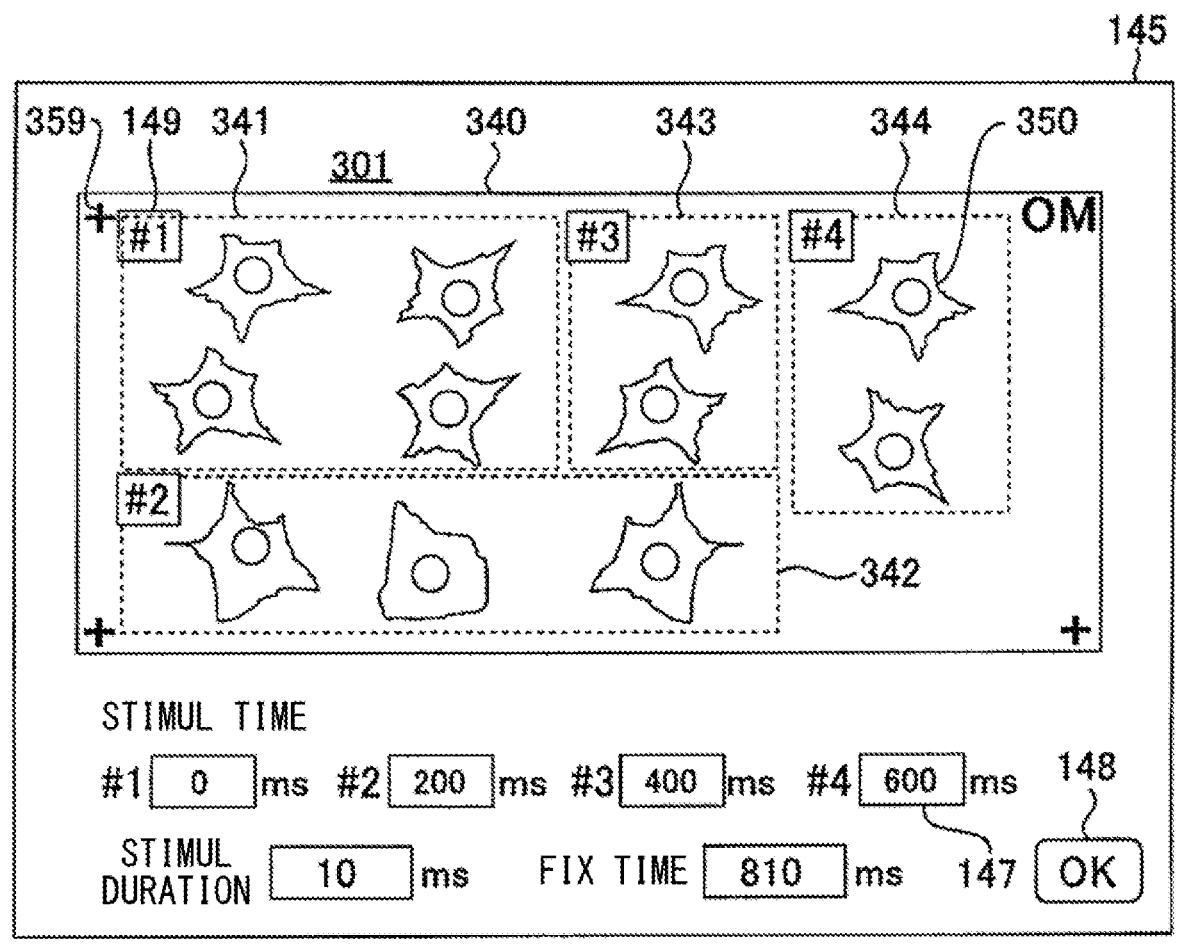
FIG. 7 is a figure showing another setting screen 145.

FIG. 7 is a figure showing another setting screen 145 displayed on the display unit 144. A user can freely designate regions in FIG. 7 in the following manner. In this case, an optical microscope-captured image OM generated by radiating excitation light from the first light source 251 onto the sample 301, and capturing an image of the sample 301 with the image-capturing unit 120 is displayed on the setting screen 145. A user uses a mouse as one example of the input unit 142 to designate regions on the captured image OM by dragging and so on. In the example shown in FIG. 7, the state where four rectangular regions are designated on the setting screen 145 by a user using a mouse is shown. Furthermore, input windows 147 for stimulation duration, fixation duration and stimulation times corresponding to respective regions as photostimulation conditions are represented. By adding "OM" to the captured image on the setting screen 145, it is represented that the captured image is acquired by an optical microscope.

On the setting screen 145 shown in FIG. 7, the captured image OM of the sample 301 acquired through the image-capturing unit 120, and dotted lines indicating the regions 341, 342, 343, 344 set by a user and labels 149 identifying the regions on the image of the sample 301 are displayed. Furthermore, stimulation duration and fixation duration set by a user and a stimulation time set for each of the regions 341, 342, 343, 344 are displayed.

Next, the control unit 140 stores, in association with each other, information identifying individual regions such as the above-mentioned labels 149 set for the sample 301 at Step S103, information on the positions of the regions, information on photostimulation conditions set for the respective regions, that is, at least stimulating light radiation times (Step S105). The information on the positions of the regions are coordinates on the support 340 relative to the position indicators 359 of the support 340 which are used as reference points, for example. Thereby, after an image of an observation sample prepared by the sample preparation system 100 is captured by an electron microscope, the captured image acquired by the electron microscope can be evaluated in association with photostimulation conditions of respective regions.

Next, the inverted microscope 110 of the sample preparation system 100 may be used to capture an image of the state of the sample 301 before stimulation (Step S106). In this case, the optical microscope-captured image OM is generated by radiating excitation light from the first light source 251 onto the sample 301, and capturing an image of the sample 301 with the image-capturing unit 120. If to obtain an image-capturing result of the sample 301 after stimulation is the only purpose, Step S106 may be omitted. In addition, up to this step, the first illuminating unit 150 and fixing unit 160 may not be joined with the inverted microscope 110.

In the following paragraphs, stimulation and fixation of the sample are explained (Step S107 to Step S111). The control unit 140 controls the third light source 253 or the like such that stimulation of the sample 301 is executed under photostimulation conditions set at Step S104 for each of the regions set at Step S103 (Step S107). The control unit 140 controls the DMD 290 or the like such that stimulating light is radiated onto the regions 341, 342, 343, 344 based on photostimulation conditions set region-by-region shown in FIG. 5. Specifically, the control unit 140 controls the third light source 253, the DMD 290 or the like such that the region 341 is irradiated with stimulating light, 200 milliseconds thereafter, the region 342 is irradiated with stimulating light, 200 milliseconds thereafter, the region 343 is irradiated with stimulating light, and further 200 milliseconds thereafter, the region 344 is irradiated with stimulating light. Based on the above-mentioned photostimulation conditions, stimulating light radiation duration is 10 milliseconds for the respective regions.

Figure 8:
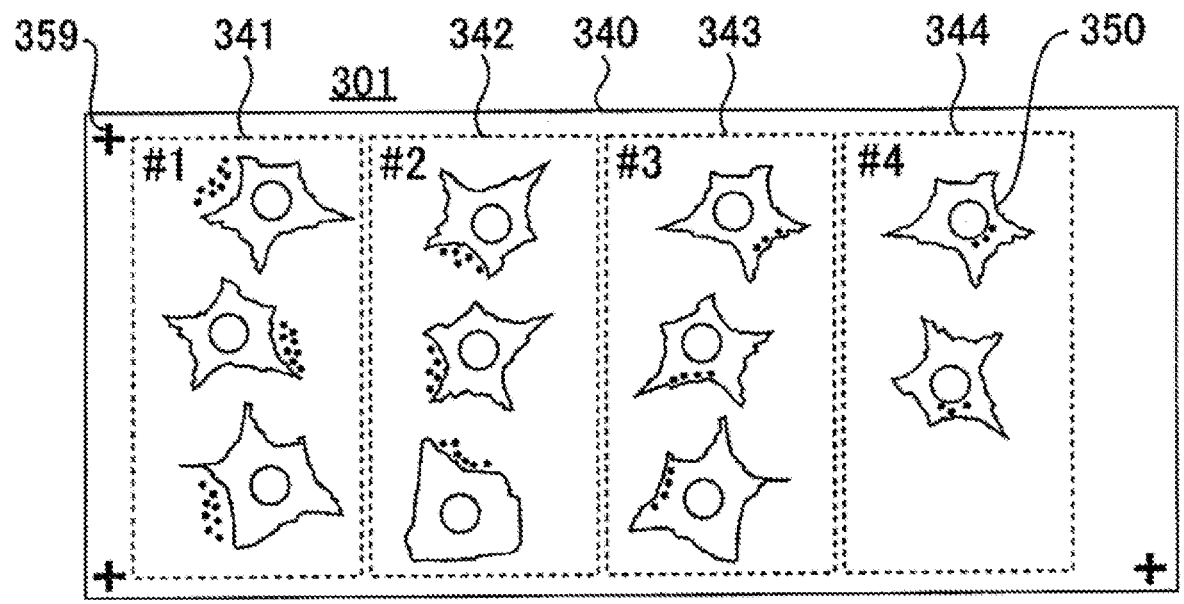
FIG. 8 is a schematic diagram showing the state of the stimulated sample 301.

FIG. 8 is a figure showing the state of the sample 301 that is fixed 810 milliseconds after radiation of stimulating light onto the first region 341 at Step S108 after being stimulated under the photostimulation conditions set at Step S107.

The example shown in the figure schematically shows an example of photostimulation in which caged compounds are irradiated with light to be uncaged and thereby activated, and a particular reaction is triggered in cells. In the region 341 photically stimulated at the earliest time, an information transmitter such as protein, for example, is released from cells 350 as a result of the cells 350 reacting to the uncaged substance. In addition, in the region 344 that is photically stimulated at the last time, an information transmitter of cells 350 is still staying within the cells 350.

Figure 10:
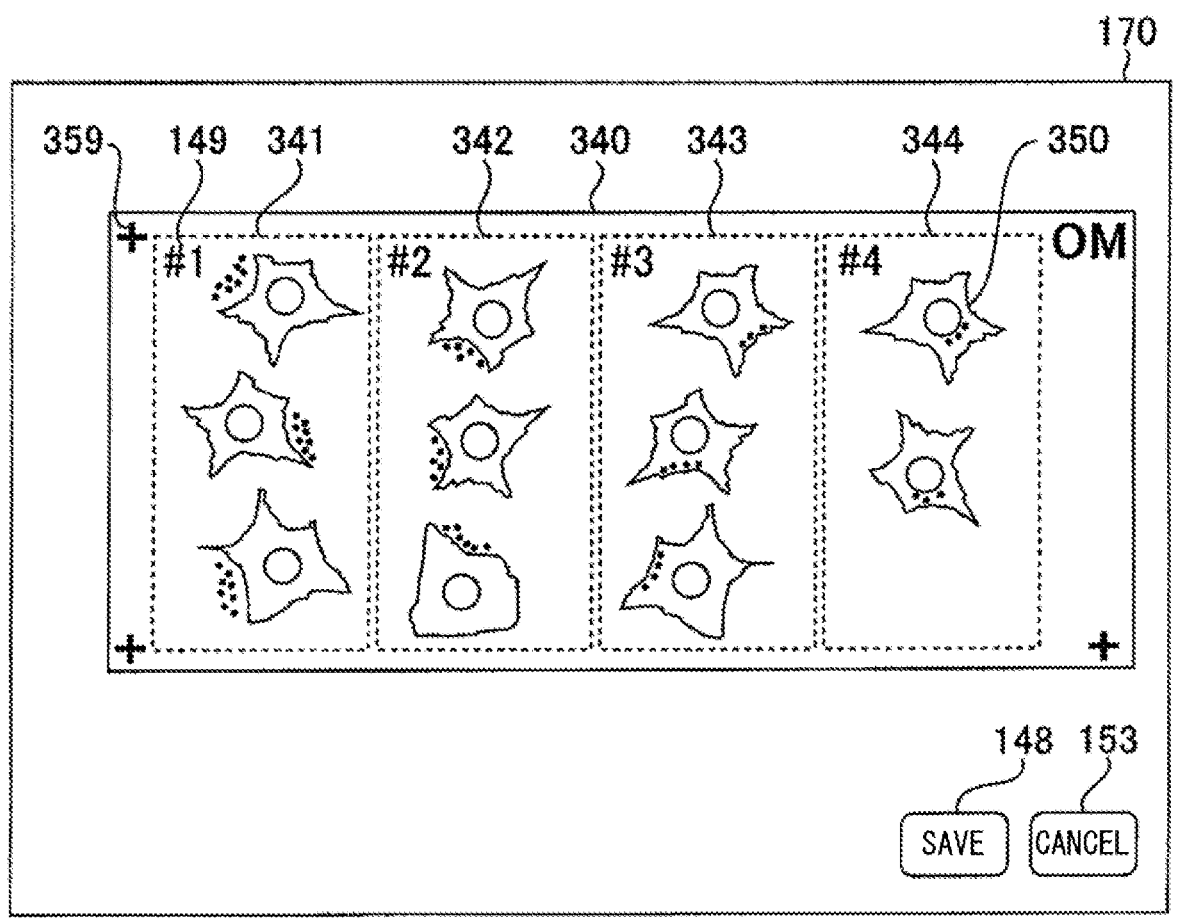
FIG. 10 is a figure showing a display screen 170.

The inverted microscope 110 may be used to capture an image of the sample 301 after stimulation (S108). FIG. 10 is a display screen 170 showing the state of the sample 301 captured at Step S108.

In this case, similar to Step 106, the optical microscope-captured image OM is generated by radiating excitation light from the first light source 251 onto the sample 301, and capturing an image of the sample 301 with the image-capturing unit 120. On the display screen 170, the captured image OM including the regions 341, 342, 343, 344 is displayed together with the characters "OM" indicating that the captured image was acquired by an optical microscope. In addition, a label 149 indicating the position in the sample 301 is added to each of the regions 341, 342, 343, 344. A user can save the optical microscope-captured images OM by pressing a save button 148 after checking the captured image on the display screen 170. In addition, a user may discard the captured image by pressing a cancel button 153.

Next, the control unit 140 controls the fixing unit 160 to fix the sample 301 following the conditions set at Step S103 (Step S109). With this process, cells in the states corresponding to temporal differences between times at which stimulating light is radiated are fixed. One example a method of fixing the sample 301 is freezing-fixation. In freezing-fixation, the sample 301 is immersed in a cooling medium such as liquid nitrogen, the sample 301 is frozen in a short time, and a biological reaction, a chemical reaction or the like in the sample 301 is stopped.

Figure 9:
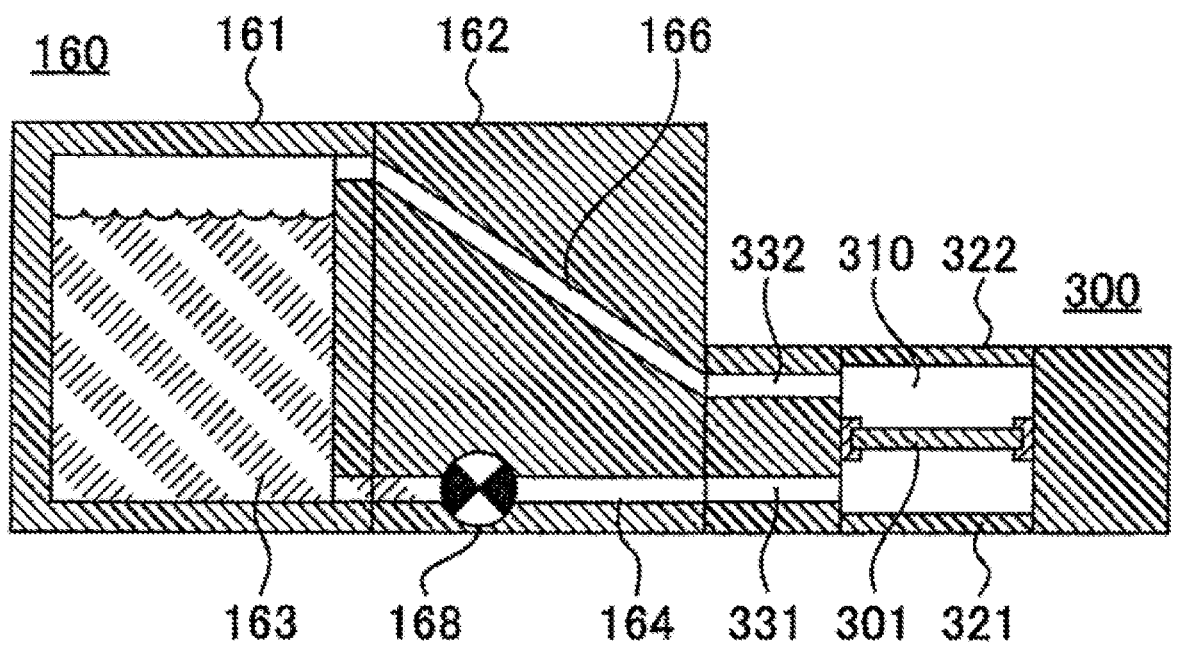
FIG. 9 is a schematic cross-sectional view of a sample holder 300 and a fixing unit 160.

FIG. 9 is a schematic cross-sectional view of the sample holder 300 and the fixing unit 160 joined together in the sample preparation system 100. The sample holder 300 houses the sample 301 at Step S102 mentioned above. In addition, the fixing unit 160 fixes the sample 301 at Step S109 mentioned above. These sample holder 300 and fixing unit 160 are joined together at the stage 112 of the sample preparation system 100.

The sample holder 300 has a cavity 310 and a pair of transparent windows 321, 322. Thereby, excitation light is radiated from the first illuminating unit 150 through the transparent window 321 onto the sample 301, and an image of light from the sample 301 can be optically captured with the image-capturing unit 120 through the transparent window 321. Furthermore, stimulating light can be radiated from the first illuminating unit 150 through the transparent window 321 onto the sample 301 housed in the sample holder 300.

The cavity 310 is formed penetrating the sample holder 300 in the height direction in the figure, and houses the sample 301 at the approximately middle in the height direction in the figure. In addition, the upper surface and lower surface, in the figure, of the cavity 310 that are opposite to each other are sealed air-tight by the transparent windows 321, 322 so that the sample 301 can be observed by the inverted microscope 110. In this manner, the sample 301 is held by the sample holder 300 at Step S102.

Furthermore, the sample holder 300 has an inlet 331 and outlet 332 at a lateral surface thereof. The inlet 331 allows the cavity 310 to communicate with the outside at a position lower than the sample 301 in the direction of gravity. The outlet allows the cavity 310 to communicate with the outside at a position higher than the sample 301. By pouring or discharging a coaling medium through these inlet 331 and outlet 332, the sample 301 held in the cavity 310 can be freeze-fixed at the sample holder 300.

The fixing unit 160 has a refrigerant container 161 and a joining portion 162. The refrigerant container 161 houses a cooling medium 163 such as liquid nitrogen. The capacity of the refrigerant container 161 is larger than the capacity of the cavity 310 in the sample holder 300, and an amount of the cooling medium 163 that can fill up the cavity 310 is housed in the refrigerant container 161.

The joining portion 162 has a pair of flow channels 164, 166 and a valve 168. One end of each of the flow channels 164, 166 communicates with either the inlet 331 or outlet 332 of the sample holder 300. The other end of each of the flow channels 164, 166 communicates with the inside of the refrigerant container 161. At least in the lower flow channel 164, the valve 168 blocks or opens up to allow a flow of the cooling medium 163 in the flow channel 164 following an instruction of the control unit 140.

If the valve 168 is opened following an instruction received from the control unit 140 in the state where the refrigerant container 161 and sample holder 300 are joined by the joining portion 162 as mentioned above, the cooling medium 163 flows from the refrigerant container 161 through the lower flow channel 164 into the cavity 310. In addition, air or the like that was initially filling the cavity 310 is pushed toward the refrigerant container 161 side through the upper flow channel 166.

Thereby, the cavity 310 is filled with the cooling medium 163, and the entire sample 301 is freeze-fixed in a short time. In this manner, at Step S109, the entire sample 301 having the plurality of regions 341, 342, 343, 344 is fixed at once following an instruction of the control unit 140.

In addition, the sample 301 may be fixed by light radiation using a composition that forms crosslinks upon radiation of light at a particular wavelength. Furthermore, a process of chemically stopping a reaction to photostimulation of the sample 301 may be executed. In such a case, a photoresponsive substance or caged compound that suppresses photoresponse by photostimulation may be used as a method of stopping a reaction.

An image of the sample 301 after fixation may be captured using the inverted microscope 110 (S110). In this case, the optical microscope-captured image OM of the sample 301 after fixation which is like the one shown in FIG. 10 and is captured by the image-capturing unit 120 as explained with reference to Step S108 is obtained.

Next, a process for capturing an image of the fixed sample 301 with an electron microscope is executed (Step S111). Here, the process for image-capturing in electron microscope observation includes embedding cells after being frozen in a resin and staining them. In the staining, heavy metal may be used for observation of X-rays. In addition, if image-capturing is performed using a transmission electron microscope, a process of making a sample thin may also be included in the above-mentioned process.

Next, an image of the prepared sample 301 for image-capturing is captured by an electron microscope (not shown in the figure) (Step S112). As mentioned above, the single sample 301 includes the plurality of regions 341 to 344 for which lengths of time after stimulation and until fixation are different. Therefore, from the single sample 301, changes in the sample 301 after stimulation can be captured in images in association with the elapse of time. In this case, based on information of the position of an image captured by an electron microscope, it is identified in which region among the plurality of regions 341 to 344 in the sample 301 for which photostimulation conditions are set the image-capturing position is included. In this case, the image-capturing position of the electron microscope is identified relative to the position indicators 359 of the support 340 which are used as reference points. By comparing the identified image-capturing position of the electron microscope and the coordinate that is stored in the control unit 140 and identifies the range of each region 341 to 344 relative to the position indicators 359 which are used as the reference points, it is identified in which region the image-capturing position is included. The electron microscope preferably captures an image of at least one or more positions in any region of the sample 301. Captured images acquired using the electron microscope are stored in association with each among the region 341 and the like.

Furthermore, the captured images acquired using the electron microscope observation are analyzed (Step S113).

Figure 11:
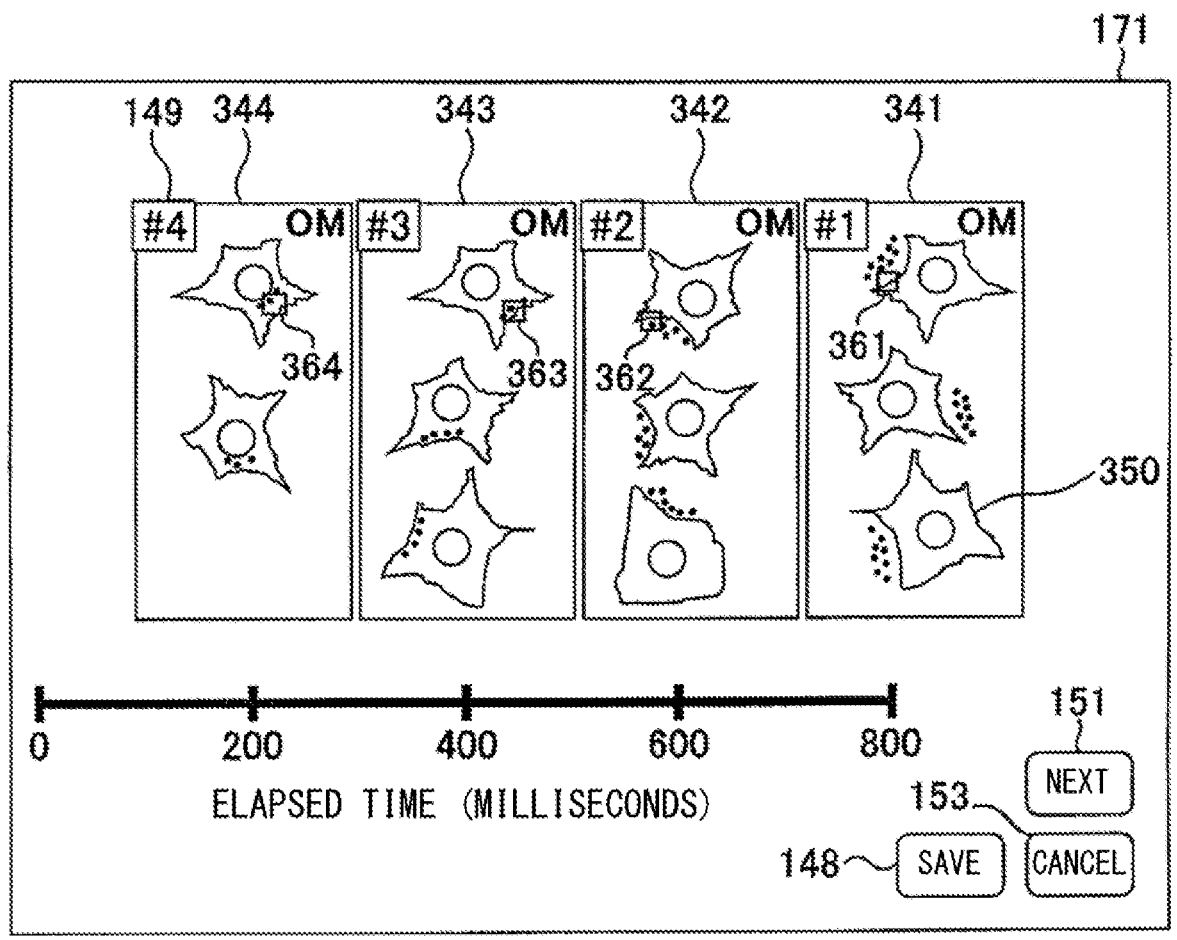
FIG. 11 is a figure showing another display screen 171.

FIG. 11 is a figure showing a display screen 171 displayed after image-capturing by the electron microscope. The display screen 171 is generated from the positional information and photostimulation condition information for each of the regions 341, 342, 343, 344 stored at Step S105, and the optical microscope-captured images OM of the sample 301 captured by the image-capturing unit 120 at Step S110 or the like. On the display screen 171, the positions of the regions 361, 362, 363, 364 images of which are captured by the electron microscope are shown in rectangular shapes on the optical microscope-captured images OM of the regions 341, 342, 343, 344 captured by the image-capturing unit 120. Furthermore, a "Next" button 151 for displaying a captured image captured by the electron microscope is displayed. A user can save an image in which an optical microscope-captured image OM and an image-capturing position at which image-capturing is performed by the electron microscope are associated with each other, by pressing the save button 148 on the display screen 171. In addition, a user may discard an image in which an optical microscope-captured image OM and an image-capturing position at which image-capturing is performed using the electron microscope are associated with each other, by pressing the cancel button 153.

Figure 12:
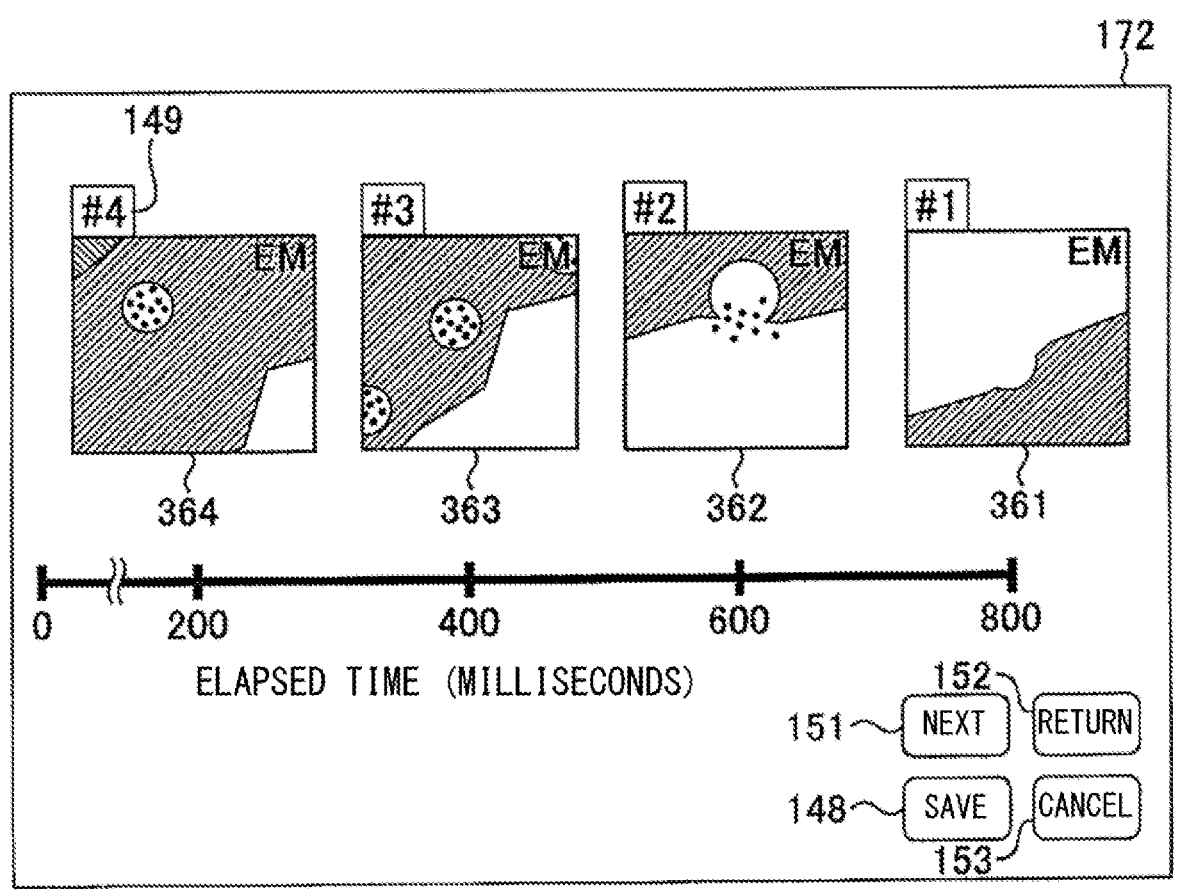
FIG. 12 is a figure showing still another display screen 172.

FIG. 12 is a figure showing a display screen 172 displayed when the "Next" button 151 shown in FIG. 11 is pressed. On the display screen 172, a label 149 corresponding to each of the regions 341, 342, 343, 344 of the optical microscope-captured images OM is added to each of captured images EM of the regions 361, 362, 363, 364 captured by the electron microscope, and additionally, the images EM are displayed after re-sorting them in the ascending order of lengths of time after photostimulation and until fixation in the sample preparation system 100. Thereby, changes in cells 350 due to the elapse of time can be readily grasped. In addition, the labels 149 associate the optical microscope-captured images OM and the electron microscope-captured images EM with each other. That the images are electron microscope-captured images is indicated by adding the characters "EM" in the captured images EM. A user can save electron microscope-captured images EM by pressing the save button 148 on the display screen 172. In addition, a user may discard an electron microscope-captured image EM by pressing the cancel button 153. In addition, a user returns to the display screen 171 shown in FIG. 11 by pressing a "Return" button 152.

In the example shown in FIG. 12, an image captured by an electron microscope shows how exocytosis in which insulin is released out of cells due to photostimulation appears. The photostimulation is performed on caged calcium (for example, NP-EGT) introduced into cells (oblique lines in the figure). If caged calcium is photically stimulated by being irradiated with light emitted from the third light source 252 (for example, 340-nm light), a phenomenon occurs in which calcium is released from the compound, and the concentration of calcium in cells rises. If the concentration of calcium in cells rises, insulin secreting granules in the cells (white circles surrounding a plurality of small black circles in the figure) migrate to the surfaces of cell membranes and merge with the cell membranes, as shown in the captured images EM of the regions 364 and 363. As shown in the captured image EM of the region 362, insulin (a plurality of small black circles in the figure) contained inside the granules is released out of the cells due to merging of the granules to the cell membranes. Furthermore, the membranes of the cells are restored as shown in the region 364.

Figure 13:
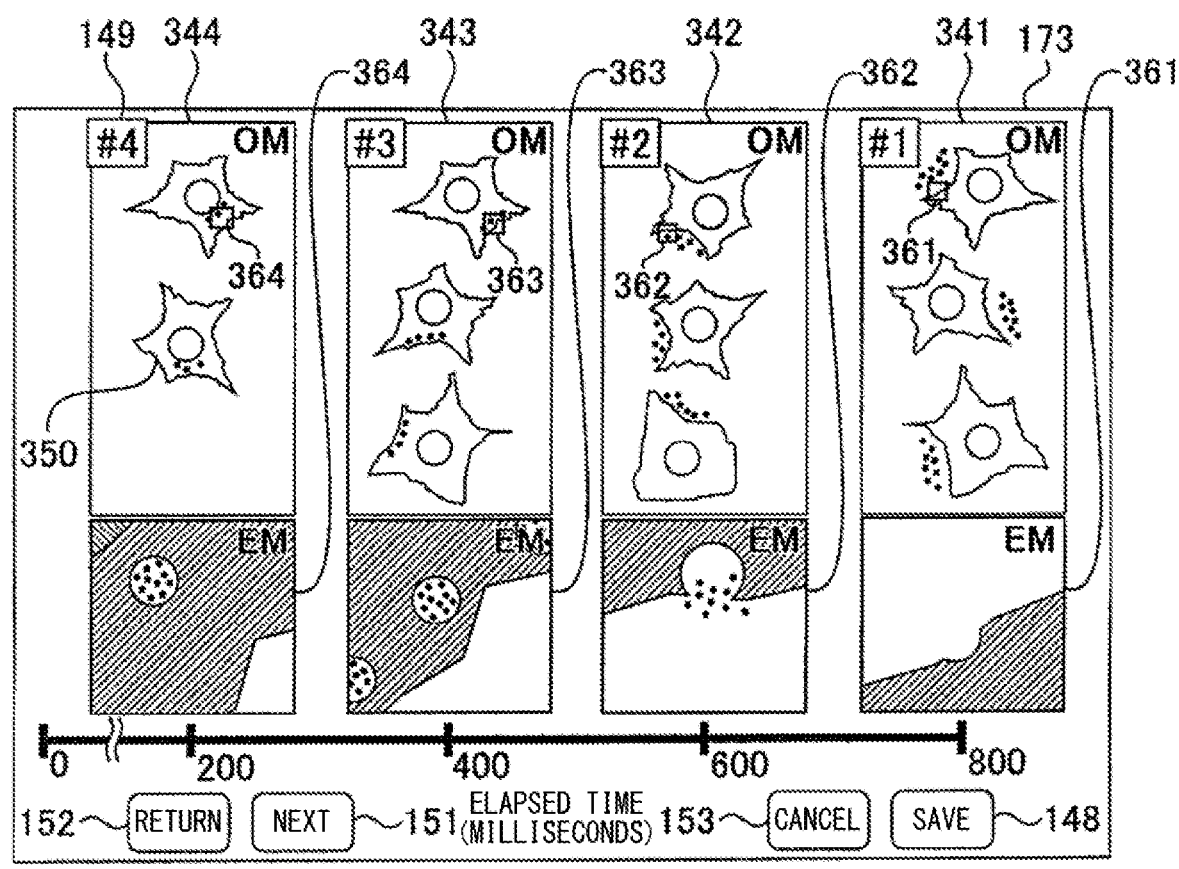
FIG. 13 is a figure showing still another display screen 173.

FIG. 13 is a figure showing a display screen 173 displayed when the "Next" button 151 shown in FIG. 12 is pressed. On the display screen 173, the captured images OM of the regions 341 to 344 shown in FIG. 11 and the captured images EM of the regions 361 to 364 shown in FIG. 12 are displayed while being visually associated vertically with each other. In other words, the optical microscope-captured images OM and the electron microscope-captured images EM are displayed at upper portions and lower portions. Thereby, temporal changes of the cells 350 based on the electron microscope-captured images EM can be readily analyzed. The display screens 171 to 173 may be displayed on the display unit 144, or may be displayed on a display apparatus of the electron microscope or a display apparatus separate from the electron microscope.

According to the embodiments shown in FIG. 1 to FIG. 13 explained so far, image of the sample 301 created under the same conditions except for temporal differences of photostimulation can be captured by an electron microscope because a plurality of regions of the sample 301 are fixed after they are photically stimulated at different times.

Figure 14:
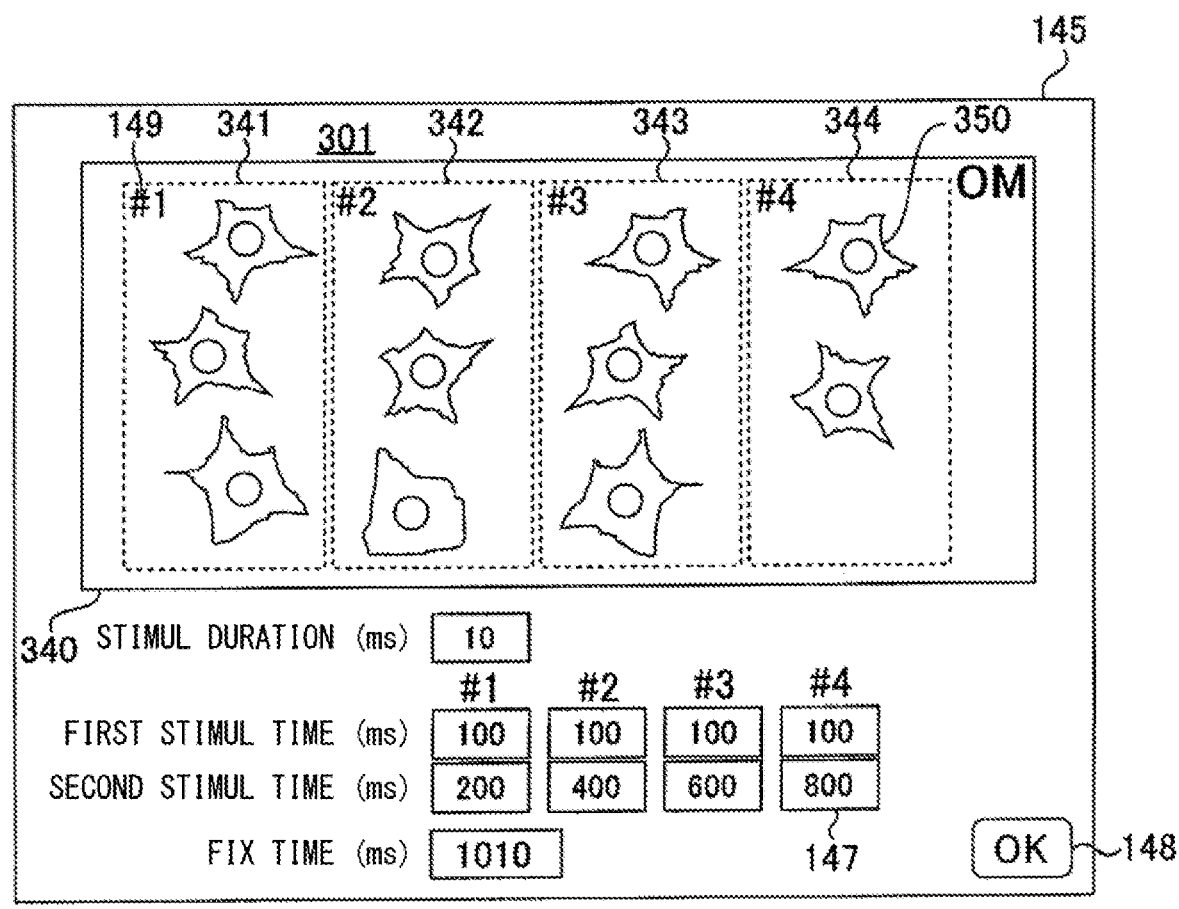
FIG. 14 is a figure showing another setting screen 145.

FIG. 14 is a figure showing another setting screen 145. On the setting screen shown in the figure, stimulation to be performed twice on the sample 301 is set. An example of the first stimulation is to activate an ion channel by giving photostimulation using a particular wavelength, for example the blue wavelength, to channelrhodopsin. An example of the second stimulation is to cause ions to flow into cells by giving photostimulation using another particular wavelength, for example the yellow wavelength, to halorhodopsin.

Corresponding to the regions 341 to 344, the setting screen 145 shown in FIG. 14 includes input windows 147 for a first stimulation time at which the first photostimulation is given and a second stimulation time at which the second photostimulation is given. By designating the stimulation times in the respective input windows 147, the first stimulation time and the second stimulation time are set region-by-region. In addition, an input window for stimulation duration during which photostimulation is given is also provided. Different values may be allowed to be input for the first stimulation duration and the second stimulation duration. In addition, for either of or both the first stimulation and the second stimulation, the stimulation times may be allowed to be set to be the same for a plurality of regions or may be allowed to be set to be different from each other. Furthermore, an input window for a fixation time at which the sample 301 is fixed is also provided.

In the example shown in FIG. 14, the first photostimulation is given to the regions 341 to 344 at the same time, and thereafter the second photostimulation is given at mutually different times.

Preferably, similar to the examples shown in FIG. 11 to FIG. 13, results obtained by capturing images of the sample 301 stimulated under the photostimulation conditions shown in FIG. 14 are also re-sorted in the ascending order of the lengths of time after photostimulation and until fixation, and are displayed together with their respective conditions.

Figure 15:
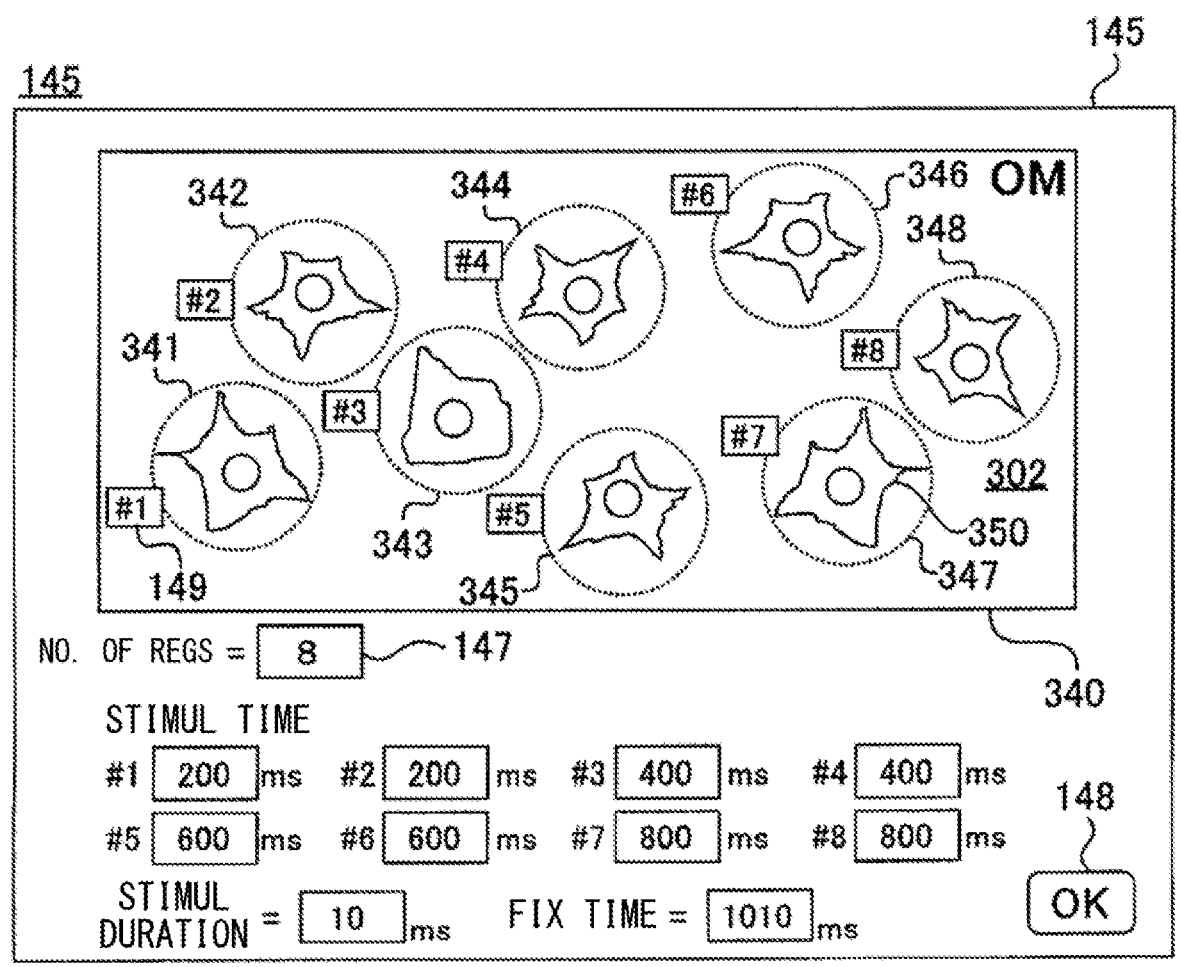
FIG. 15 is a figure showing another setting screen 145.

FIG. 15 is a figure showing another setting screen 145. In the example shown in FIG. 15, the positions of cells 350 are specified on the optical microscope-captured image OM acquired in a manner similar to that at Step S106, and regions 341, 342, 343, 344, 345, 346, 347, 348 are set to surround the respective cells 350. "8" is displayed in the input window 147, corresponding to the number of regions that were set. Furthermore, stimulation duration and fixation times, and stimulation times for the respective regions are set.

Specification of the positions of the cells 350, in other words, setting of the region 341 or the like may be set manually by a user dragging on the optical microscope-captured images OM displayed on the setting screen 145 or the like, or the control unit 140 may extract candidates automatically by image processing from the optical microscope-captured image OM captured by the image-capturing unit 120.

Because photostimulation conforming to the shapes of the cells 350 is possible according to the setting screen 145 shown in FIG. 15, radiation of stimulating light onto other regions can be prevented. Here, fluctuation in image-capturing results due to individual differences of the cells 350 can be suppressed by setting the same photostimulation conditions to a plurality of regions.

Figure 16:
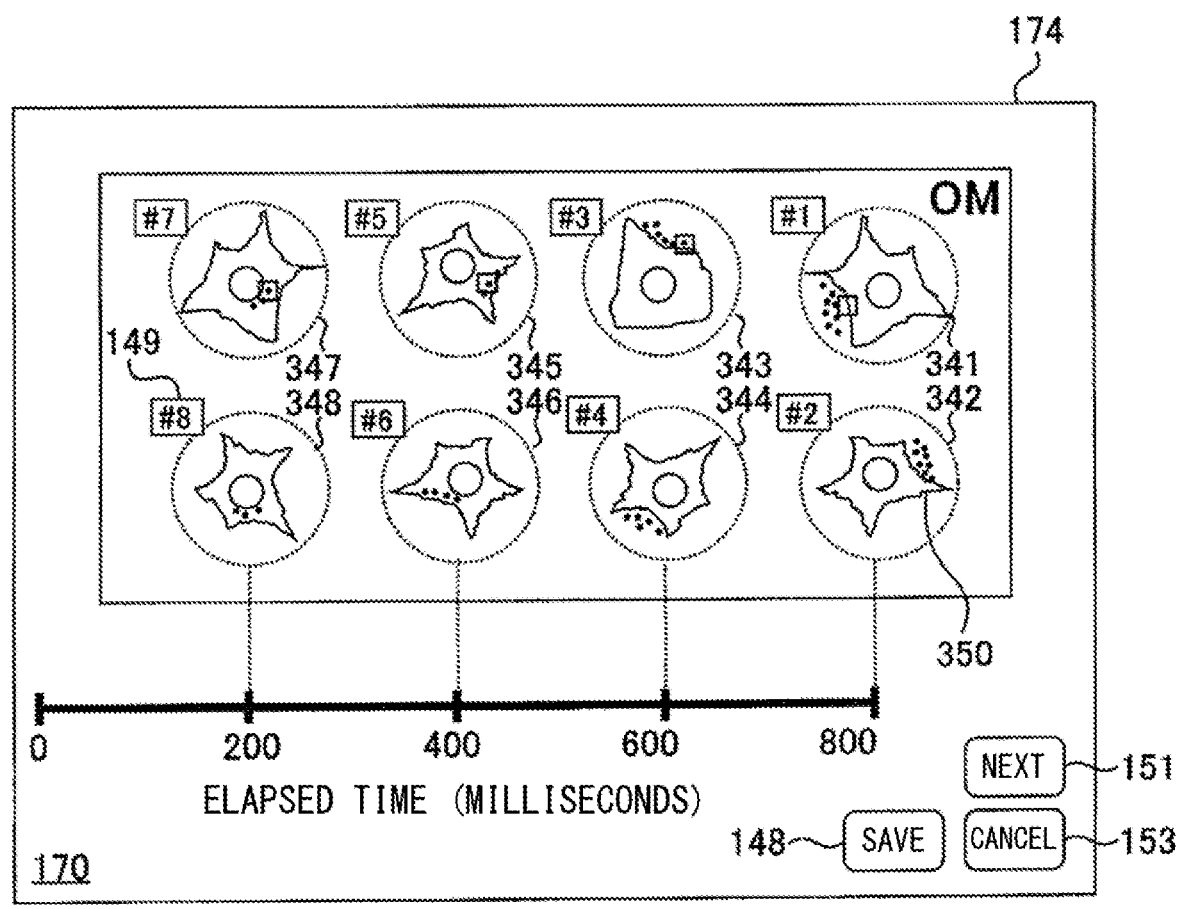
FIG. 16 is a figure showing another display screen 174.

FIG. 16 is a figure showing one example of a display screen 174 for a sample 302. The display screen 174 is generated based on images of the sample 301 captured by the image-capturing unit 120, and positional information and photostimulation condition information for each of the regions 341, 342, 343, 344 that are acquired from the control unit 140 of the sample preparation system 100.

Similar to FIG. 11, on the display screen 174, a label 149 corresponding to the arrangement, on the sample 301, of each of the regions 341 to 348 captured by the image-capturing unit 120 is added to the region, and additionally they are re-sorted in the ascending order of the lengths of time after photostimulation and until fixation in the sample preparation system 100. On the display screen 174, the positions of the regions 361, 362, 363, 364 images of which are captured by the electron microscope are shown in rectangular shapes on the optical microscope-captured image OM of the regions 341, 342, 343, 344 captured by the image-capturing unit 120.

Figure 17:
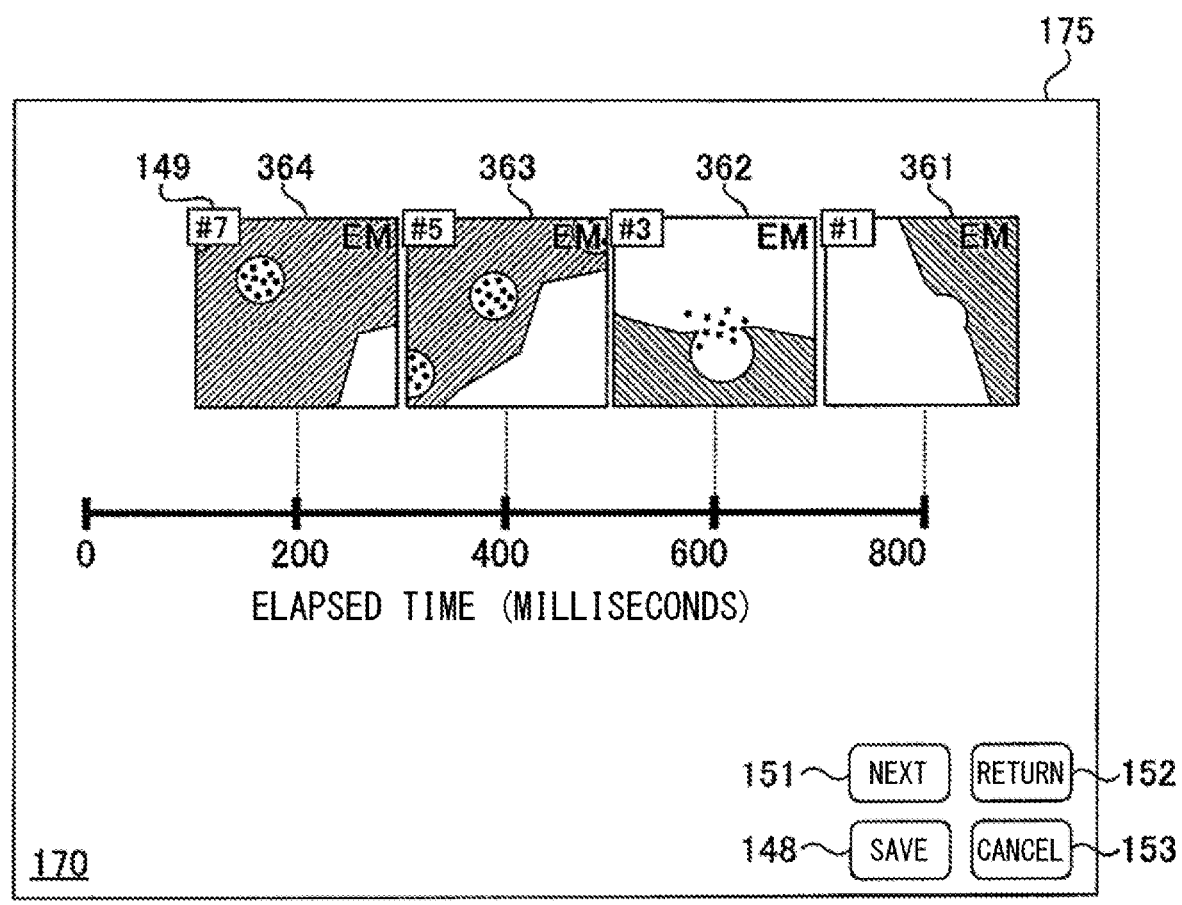
FIG. 17 is a figure showing still another display screen 175.

FIG. 17 is a figure showing a display screen 175 displayed when the "Next" button 151 shown in FIG. 16 is pressed. On the display screen 175, a label 149 corresponding to the position (arrangement) in the sample 301 is added to each of the captured images EM of the regions 361, 362, 363, 364 captured by the electron microscope, and additionally, the images EM are displayed after re-sorting them in the ascending order of lengths of time after photostimulation and until fixation in the sample preparation system 100. Thereby, changes in the cell 350 due to the elapse of time can be readily grasped. In addition, the labels 149 associate the optical microscope-captured images OM and the electron microscope-captured images EM with each other.

Figure 18:
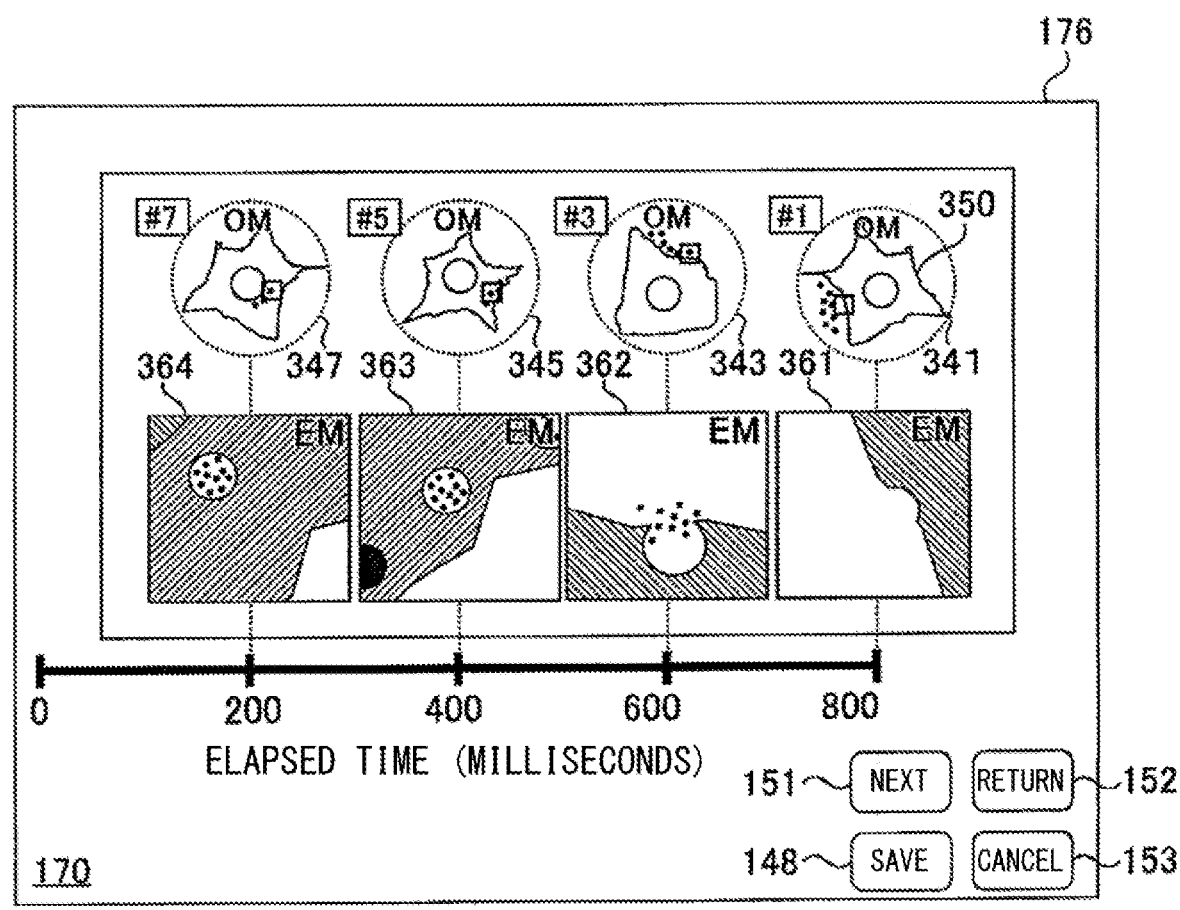
FIG. 18 is a figure showing still another display screen 176.

FIG. 18 is a figure showing a display screen 176 displayed when the "Next" button 151 shown in FIG. 17 is pressed. On the display screen 176, the captured images GM of the regions 341 to 344 shown in FIG. 16 and the captured images EM of the regions 361 to 364 shown in FIG. 17 are displayed while being associated vertically with each other. In other words, the optical microscope-captured images GM and the electron microscope-captured images EM are displayed at upper portions and lower portions. Thereby, temporal changes of the cells 350 based on the electron microscope-captured images EM can be readily analyzed.

Figure 19:
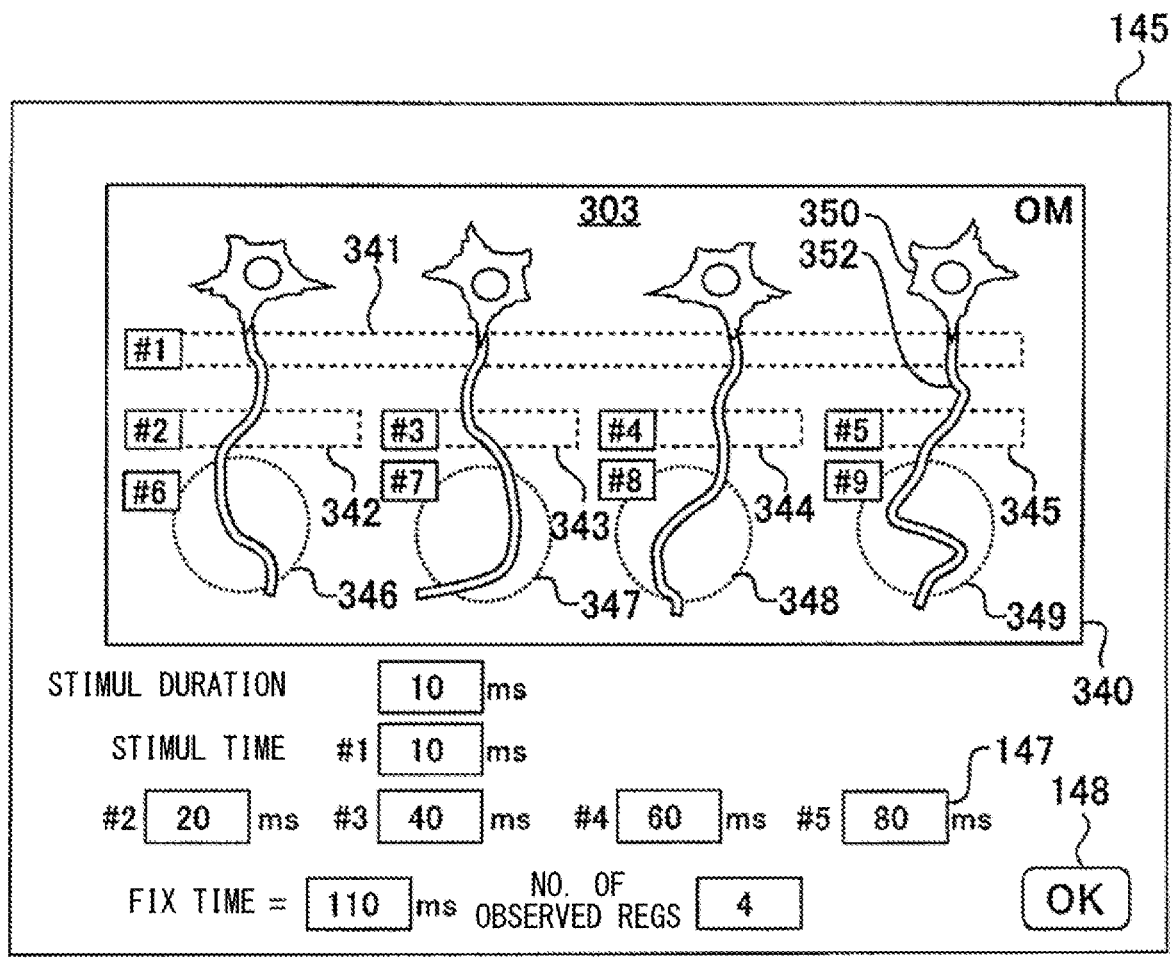
FIG. 19 is a figure showing another setting screen 145.

FIG. 19 is a figure showing the setting screen 145 for setting photostimulation conditions about a sample 303. In the sample 303, cells 350 which are a plurality of nerve cells each having an axon 352 are disposed on the support 340. In each of the cells 350, the axon 352 includes channelrhodopsin and halorhodopsin expressed by gene transfer.

In the above-mentioned sample 303, a plurality of regions 341, 342, 343, 344, 345, 346, 347, 348, 349 are designated on an optical microscope-captured image GM displayed on the setting screen 145. Among them, the region 341 designated as #1 is a region in which channelrhodopsin is given photostimulation as the first stimulation. In the example shown in FIG. 19, the region 341 includes a root portion of the axon 352 in each of the cells 350. The regions 342, 343, 344, 345 to which #2 to #5 are allocated are regions in which photostimulation is given to halorhodopsin as the second stimulation. In the example shown in FIG. 19, the regions 342 to 345 are positioned closer to the leading end side of the axons 352 than the region 341 is. Stimulation times at which stimulation is given to these regions 341 to 345 are designated on the setting screen 145. Thereby, photostimulation can be given to different regions of the same cells 350 under different stimulation conditions. In addition, an input window for stimulation duration during which photostimulation is given is also provided. Different values may be allowed to be input for the first stimulation duration and the second stimulation duration. Furthermore, an input window for a fixation time at which the sample 301 is fixed is also provided.

By radiating stimulating light at a particular wavelength onto the region 341 as the first stimulation at a designated time, ion channels at the irradiated position are activated to generate action potential and conveyed through the axons 352. Thereafter, by radiating stimulating light at another particular wavelength at times respectively set for the regions 342 to 345 as the second stimulation, ions are caused to flow into cells at the irradiated position, and conveyance of action potential is suppressed thereby.

Furthermore, on the setting screen 145, regions 346, 347, 348, 349 for image-capturing by an electron microscope are set at the further leading end side of the axons 352. These region 346, 347, 348, 349 are given labels 149, #6 to #9.

Figure 20:
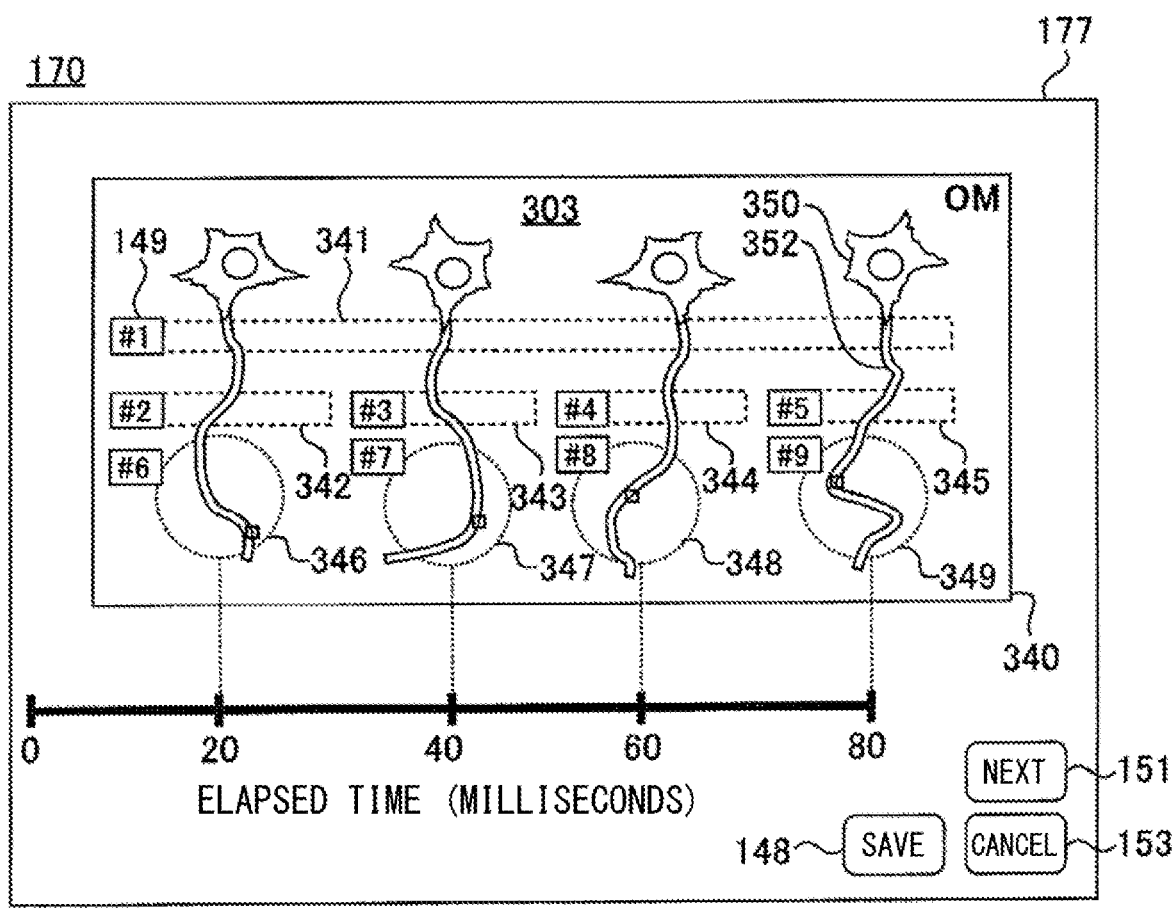
FIG. 20 is a figure showing another display screen 177.

FIG. 20 is a figure showing one example of the display screen 177 for the sample 303. The display screen 177 is generated based on the optical microscope-captured images OM of the sample 303 captured by the image-capturing unit 120, and positional information and photostimulation condition information for the regions 341 to 349 that are acquired from the control unit 140 of the sample preparation system 100.

Similar to FIG. 11, on the display screen 177, a label 149 corresponding to the arrangement in the sample 303 is added to each of the regions 341 to 349 captured by the image-capturing unit 120. Furthermore, they are re-sorted in the ascending order of the lengths of time after photostimulation and until fixation in the sample preparation system 100. Furthermore, the regions 346, 347, 348, 349 for image-capturing by an electron microscope and elapsed time after photostimulation and until fixation in the sample preparation system 100 are shown while being associated with each other by dotted lines. Furthermore, the positions of the regions 361, 362, 363, 364 images of which are capture by the electron microscope are shown in rectangular shapes on the captured images of the regions 346, 347, 348, 349 captured by the image-capturing unit 120.

Figure 21:
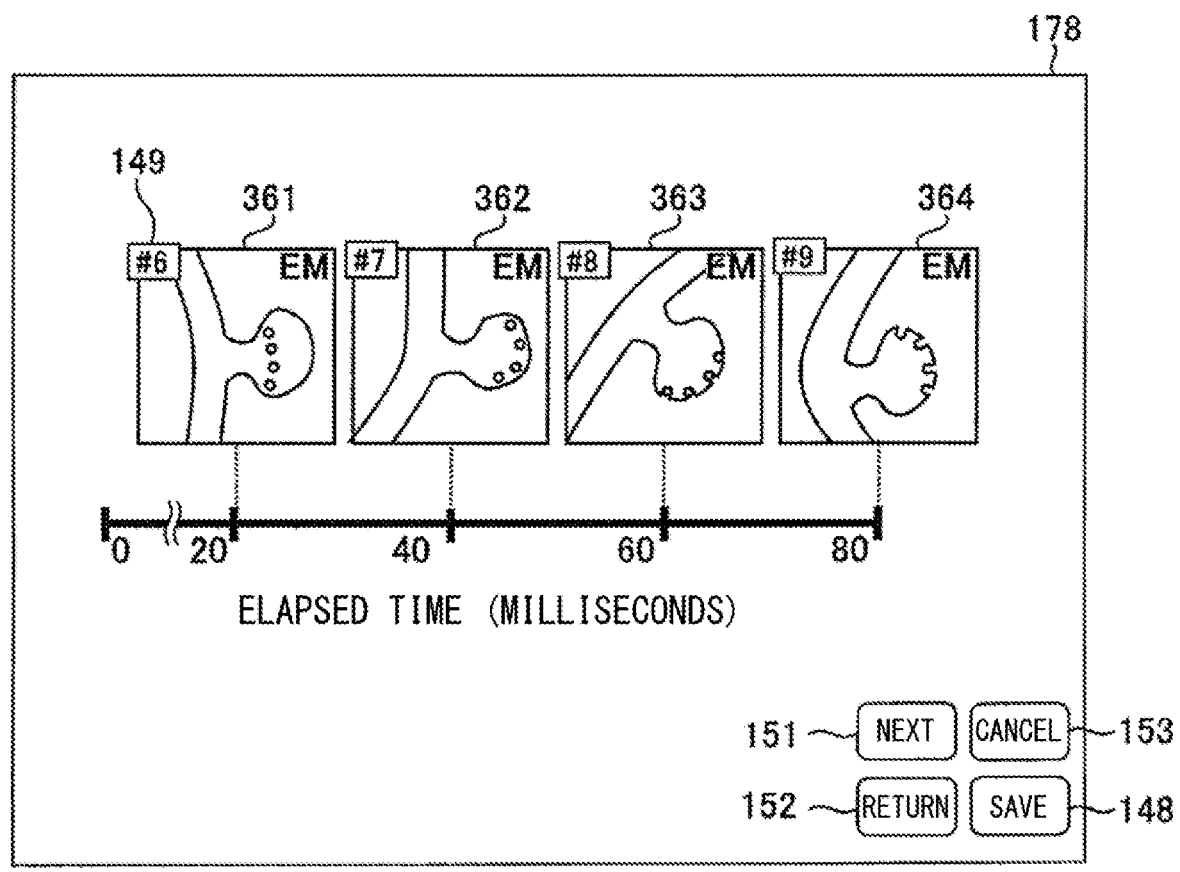
FIG. 21 is a figure showing still another display screen 178.

FIG. 21 is a figure showing a display screen 178 displayed when the "Next" button 151 shown in FIG. 20 is pressed. On the display screen 178, a label 149 corresponding to the position (arrangement) in the sample 303 is added to each of the captured images EM of the regions 361, 362, 363, 364 captured by the electron microscope, and additionally, they are displayed after re-sorting them in the ascending order of lengths of time after photostimulation and until fixation in the sample preparation system 100. Thereby, changes in the cells 350 due to the elapse of time can be readily grasped. In addition, the labels 149 associate the optical microscope-captured images OM and the electron microscope-captured images EM with each other.

FIG. 21 shows how it appears when a neurotransmitter such as acetylcholine is released out of a spine by giving photostimulation tai channelrhodopsin introduced into cells. In this case, if photostimulation is given to channelrhodopsin introduced into cells by radiating, for example, 470-nm light onto it, sodium ions flow from channels given the photostimulation into the cells. If the concentration of sodium in a cell rises, the signal triggers migration of vesicles (indicated as small white circles in the figure) including information transmitters in the spine toward a surface side of the spine as indicated in the regions 361 and 362. Furthermore, they merge with membranes at the surface of the spine as shown in the region 363. Because of the merging of the vesicles with the membranes, a neurotransmitter contained in the vesicles is released out of the spine as shown in the region 364.

Figure 22:
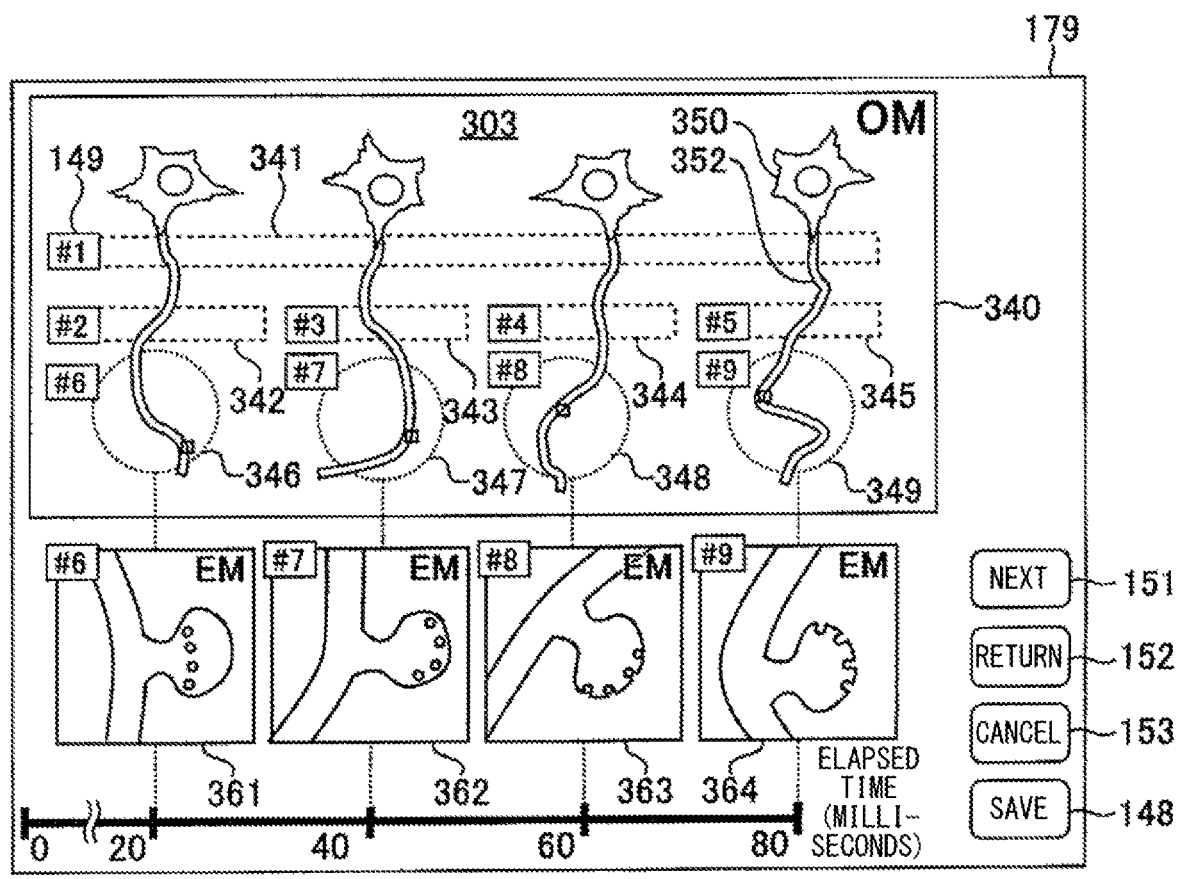
FIG. 22 is a figure showing still another display screen 179.

FIG. 22 is a figure showing a display screen 179 displayed when the "Next" button 151 shown in FIG. 21 is pressed. On the display screen 179, the captured images of the regions 346 to 349 shown in FIG. 20 and the captured images of the regions 361 to 364 shown in FIG. 21 are displayed while being associated vertically with each other. In other words, the optical microscope-captured images OM and the electron microscope-captured images EM are displayed at upper portions and lower portions. Thereby, temporal changes of the cells 350 based on the electron microscope-captured images can be readily analyzed.

Figure 23:
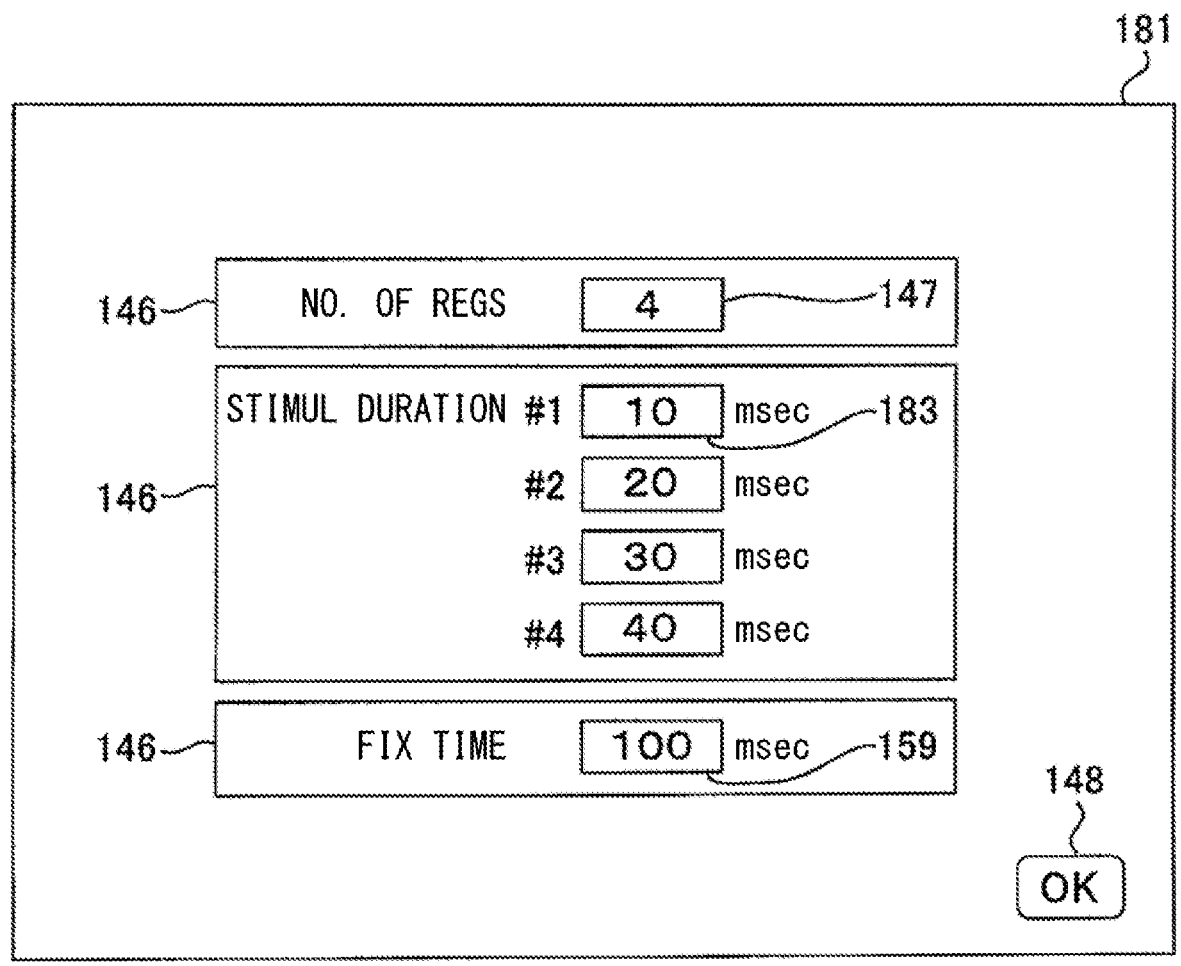
FIG. 23 is a figure showing another setting screen 181.

FIG. 23 is a figure showing another setting screen 181. On the setting screen 181, setting can be performed such that radiation of light onto a plurality of regions of the sample 301 is simultaneously started, the light is radiated for mutually different lengths of time, and the sample 301 is fixed thereby. An input window 147 for setting the number of regions is provided on the setting screen 181. Furthermore, an input window 183 for setting stimulation duration in the respective regions corresponding to the number of regions is provided. Furthermore, an input window 159 for inputting a time at which the sample 301 is fixed is provided.

Still other examples of observation targets include observation samples for fluorescence observation of cells by FRAP (Fluorescence Recovery after Photobleaching), FLIP (Fluorescence Loss in Photobleaching), FLAP (fluorescence localization after photobleaching), CALI (Chromophore-assisted laser inactivation) or the like.

In addition, the method of fixing the sample 301 is not limited to the one using the fixing unit 160 shown in FIG. 9. Instead of this, the sample 301 may be fixed by providing a bath filled with a liquid refrigerant in advance, moving the sample 301 from the sample holder 300 to the bath by an arm or the like and causing the sample 301 to be immersed in the bath.

Instead of or in addition to the setting screen 145 shown in FIG. 5, FIG. 7, FIG. 14 or other figures, a setting screen for accepting setting of the order of the step of radiating light onto each region of the sample and the fixation step may be displayed.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A sample preparation method comprising:
   irradiating a first region of a sample with light at a time t1;
   irradiating a second region different from the first region with the light at a time t2 after the time t1; and
   fixing the sample at a time t3 after the time t2, wherein
   the first region and the second region are automatically selected by a controller in response to a first input by a user indicating the number of regions to be irradiated with the light, and
   the time t2 and the time t3 are automatically set by the controller in response to a second input by the user indicating an irradiation interval of time.

2. The sample preparation method according to claim 1, wherein the light radiated onto the first region and the second region is stimulating light for photically stimulating the sample.

3. The sample preparation method according to claim 2, wherein the first region and the second region are fixed after mutually different elapsed times after the first region and the second region are irradiated with the stimulating light.

4. The sample preparation method according to claim 1, further comprising capturing an image of the sample using an optical microscope after the irradiating the second region.

5. The sample preparation method according to claim 1, wherein the fixing is performed by freezing.

6. The sample preparation method according to claim 1, wherein the fixing is performed by light radiation.

7. The sample preparation method according to claim 1, wherein the fixed sample is a sample to be observed for a change over time caused by the irradiation using an electron microscope.

8. The sample preparation method according to claim 7, comprising capturing an image of the sample using an electron microscope after the fixing.

9. The sample preparation method according to claim 8, further comprising:
   capturing an image of the sample using an optical microscope after the irradiating the second region; and
   displaying the image of the sample captured by using the optical microscope and the image of the sample captured by using the electron microscope, in association with each other.

10. The sample preparation method according to claim 1, wherein the first region and the second region are irradiated with light at mutually different light intensities.

11. The sample preparation method according to claim 1, further comprising
    irradiating a third region different from the first region and the second region with the light after the time t2 and before the time t3, wherein
    a difference between the time t1 and the time t2 is the same as a difference between the time t2 and the time t3.

12. A sample preparation method comprising:
    irradiating a first region of a sample and a second region different from the first region with light at a time t1;
    irradiating the first region with light at a time t2 after the time t1;
    irradiating the second region with the light at a time t3 after the time t2; and
    fixing the sample at a time t4 after the time t3.

13. A sample preparation method comprising:
    irradiating a first region of a sample and a second region different from the first region with light for mutually different lengths of time after simultaneously starting the irradiation of light; and
    fixing the sample after the irradiating.

* * * * *